(12) United States Patent
Park

(10) Patent No.: US 11,377,489 B2
(45) Date of Patent: Jul. 5, 2022

(54) DUAL-TARGETING ANTIBODY TARGETING SCF AND GALECTIN-1 AND USE THEREOF

(71) Applicant: NOVELTY NOBILITY INC., Seongnam-si (KR)

(72) Inventor: Sang Gyu Park, Suwon-si (KR)

(73) Assignee: NOVELTY NOBILITY INC., Seongnam-si (KR)

( * ) Notice: Subject to any disclaimer, the term of this patent is extended or adjusted under 35 U.S.C. 154(b) by 79 days.

(21) Appl. No.: 16/760,513

(22) PCT Filed: Oct. 30, 2018

(86) PCT No.: PCT/KR2018/013016
§ 371 (c)(1),
(2) Date: Apr. 30, 2020

(87) PCT Pub. No.: WO2019/088658
PCT Pub. Date: May 9, 2019

(65) Prior Publication Data
US 2021/0198351 A1    Jul. 1, 2021

(30) Foreign Application Priority Data

Oct. 31, 2017 (KR) .................. 10-2017-0143816
Oct. 24, 2018 (KR) .................. 10-2018-0127615

(51) Int. Cl.
*C07K 16/24* (2006.01)
*C12N 15/13* (2006.01)
*A61K 39/00* (2006.01)

(52) U.S. Cl.
CPC ........ *C07K 16/24* (2013.01); *A61K 2039/505* (2013.01); *C07K 2317/565* (2013.01)

(58) Field of Classification Search
None
See application file for complete search history.

(56) References Cited

U.S. PATENT DOCUMENTS

| 2011/0142840 A1 | 6/2011 | Van Der Horst et al. |
| 2013/0011409 A1 | 1/2013 | Shipp et al. |
| 2017/0073395 A1 | 3/2017 | Finlay et al. |

FOREIGN PATENT DOCUMENTS

| WO | 2015173756 A2 | 11/2015 |
| WO | 2016141387 A1 | 9/2016 |

OTHER PUBLICATIONS

KIPO (ISA/KR), "International Search Report and Written Opinion for PCT Application No. PCT/KR2018/013016", KR, dated Mar. 14, 2019.

*Primary Examiner* — Christine J Saoud
*Assistant Examiner* — Jon M Lockard
(74) *Attorney, Agent, or Firm* — Locke Lord LLP; Tim Tingkang Xia, Esq.

(57) ABSTRACT

The present invention relates to a dual-targeting antibody targeting stem cell factor (SCF) and galectin-1 and a composition for preventing or treating angiogenesis-related diseases comprising the same. The present invention provides a dual-targeting antibody derived from a human monoclonal antibody which may effectively inhibit angiogenesis by simultaneously neutralizing SCF and galectin-1 involved in angiogenesis, and a pharmaceutical composition for preventing or treating angiogenesis-related diseases comprising the antibody. The dual-targeting antibody according to the present invention may effectively prevent or treat angiogenesis-related diseases by simultaneously neutralizing two targets involved in angiogenesis wherein the angiogenesis-related diseases cause hemorrhaging by blood vessels changing due to abnormal angiogenesis and thus increasing the permeability thereof.

11 Claims, 16 Drawing Sheets

Specification includes a Sequence Listing.

```
GAT GTT GTG ATG ACT CAG
 D   V   V   M   T   Q

TCT CCA CTC TCC CTG CCC GTC ACC CTT GGA CAG CCG GCC TCC ATC
 S   P   L   S   L   P   V   T   L   G   Q   P   A   S   I

CDR1
TCC TGC AGG TCT AGT [CAA AGC CTC GTA TAC AGT GAT GGA AAC ACC
 S   C   R   S   S   Q   S   L   V   Y   S   D   G   N   T

TAC] TTG AAT TGG TTT CAG CAG AGG CCA GGC CAA TCT CCA AGG CGC
 Y    L   N   W   F   Q   Q   R   P   G   Q   S   P   R   R

CDR2
CTA ATT TAT [AAG GTT TCT] AAC CGG GAC TCT GGG GTC CCA GAC AGA
 L   I   Y   K   V   S    N   R   D   S   G   V   P   D   R

TTC AGC GGC AGT GGG TCA GGC ACT GAT TTC ACA CTG AAA ATC AGC
 F   S   G   S   G   S   G   T   D   F   T   L   K   I   S

CDR3
AGG GTG GAG GCT GAG GAT GTT GGG GTT TAT TAC TGC [ATG CAA GGT
 R   V   E   A   E   D   V   G   V   Y   Y   C   M   Q   G

ACA CAC TGG CCT CTT] TCG GCG GAG GGA CCA AGG TGG AGA TCA AAC
 T   H   W   P   L    S   A   E   G   P   R   W   R   S   N
```

FIG. 5

```
CAG GTG CAG CTG GTG GAG TCT GGG GGA GGC GTG
 Q   V   Q   L   V   E   S   G   G   G   V

GTC CAG CCT GGG AGG TCC CTG AGA CTC TCC TGT GTA GCG TCT [GGA
 V   Q   P   G   R   S   L   R   L   S   C   V   A   S   G
                                CDR1
TTC ACC TTC AGT AGC TAT GGC] ATG CAC TGG GTC CGC CAG GCT CCA
 F   T   F   S   S   Y   G    M   H   W   V   R   Q   A   P
                                                 CDR2
GGC AAG GGG CTG GAC TGG GTG GCA GTT [ATA TGG TAT  GAT GGA AGT
 G   K   G   L   D   W   V   A   V   I   W   Y    D   G   S

AAT AAC] GAC TAT GCA GAC TCC GTG AAG GGC CGA TTC ACC ATC TCC
 N   N    D   Y   A   D   S   V   K   G   R   F   T   I   S

AGA GAC AAT TCC AAG AAC ACA CTG TAT CTA CAA ATG AAC AGC CTG
 R   D   N   S   K   N   T   L   Y   L   Q   M   N   S   L
                                              CDR3
AGA GCC GAG GAC ACG GCT GTA TAT TAC TGT [GCG AGA GGG CAA AAT
 R   A   E   D   T   A   V   Y   Y   C    A   R   G   Q   N

TAC TAT GGT TTG GGG AGT TAT TTC TTT GAC TAC] TGG GGC CAG GGA
 Y   Y   G   L   G   S   Y   F   F   D   Y    W   G   Q   G

ACC CTG GTC ACC
 T   L   V   T
```

FIG. 6

DUAL-TARGETING ANTIBODY TARGETING SCF AND GALECTIN-1 AND USE THEREOF

TECHNICAL FIELD OF THE INVENTION

The present disclosure relates to a dual-targeting antibody that targets a stem cell factor (SCF) and galectin-1 and a composition for prevention or treatment of angiogenesis-related diseases containing the same.

BACKGROUND OF THE INVENTION

The SCF (stem cell factor) is known as a factor deeply involved in differentiation of blood cells, sperm, and melanocytes. The SCF is mainly produced in fibroblast and endothelial cells and is known to have increase in expression and secretion thereof in a hypoxia state to promote angiogenesis. Further, the galectin-1 is a factor that is secreted in a hypoxia state and binds to the Vascular Endothelial Growth Factor (VEGF) receptor as a representative protein that regulates angiogenesis, thereby to induce angiogenesis. Even when the VEGF is inhibited, blood vessels are induced by the galectin-1 as a new ligand.

Angiogenesis means that new micro vessels are created from existing blood vessels already present due to angiogenesis factors in the body. When cells grow to some extent, they secrete substances that stimulate angiogenesis. Conversely, when the substance is released too much, they secrete substances that inhibit the release. Feedback is used to balance angiogenesis.

Blood vessels of most adults rarely divide. Normal angiogenesis is extremely rare in the adult. Abnormal angiogenesis leads to bleeding causing diseases due to altered blood vessels and thus increased permeability. Examples of the diseases may comprise age-related macular degeneration, diabetic retinopathy, choroidal neovascularization, glaucoma retinitis pigmentosa, retinopathy of prematurity, glaucoma, corneal dystrophy, retinoschises, rheumatoid arthritis, psoriasis, tumor metastasis, and delayed wound healing.

In particular, angiogenesis in the cornea in the above diseases may impair eye transparency, thus resulting in loss of vision. Angiogenesis in the retina leads to abnormal blood vessels resulting in blood exudation, thereby to cause blindness due to degeneration of the retinal cells. Thus, angiogenesis in the eye is not a desirable phenomenon and is preferably suppressed as much as possible. As such, diseases caused by abnormal angiogenesis may be cured by suppressing neovascularization.

For this reason, studies on the treatment of angiogenesis-related diseases using angiogenesis inhibitors are being conducted. Many angiogenesis promoters and angiogenesis inhibitors such as vascular endothelial cell growth, migration, differentiation and capillary formation have been found to be involved in angiogenesis. Angiogenesis inhibitors are activated against the activity of angiogenesis promoters that are necessary for angiogenesis. Angiogenesis inhibitors that are naturally present in the body are less toxic and may be used to inhibit pathological angiogenesis and thus, many drugs in this regard are being developed.

The present inventors have diligently sought to find therapeutic agents for angiogenesis-related disease. Thus, we have confirmed that the stem cell factor (SCF) and galectin-1 promote angiogenesis, and that inhibition of expression of the SCF and galectin-1 inhibits neovascular expression. Thus, the present inventors have produced a dual-targeting antibody capable of simultaneously neutralizing the SCF and galectin-1. In this way, the present disclosure has been completed.

SUMMARY OF THE INVENTION

Technical Problem

A purpose of the present disclosure is to provide a dual-targeting antibody that specifically binds to the SCF (Stem Cell Factor) and the galectin-1.

Another purpose of the present disclosure is to provide DNA encoding the dual-targeting antibodies that specifically bind to the SCF and galectin-1.

Another purpose of the present disclosure is to provide a pharmaceutical composition for prevention or treatment of angiogenesis-related diseases, the composition containing the dual-targeting antibodies that specifically bind to the SCF and the galectin-1.

Another purpose of the present disclosure is to provide a method for preventing or treating the angiogenesis-related disease, the method comprising administering the dual-targeting antibody that specifically binds to the SCF and galectin-1 to a subject in need thereof.

Another purpose of the present disclosure is to provide a composition for simultaneous detection of the SCF and the galectin-1, the composition containing the dual-targeting antibody that specifically binds to the SCF and galectin-1.

Technical Solution

In order to achieve the above purposes, the present disclosure provides a dual-targeting antibody that specifically binds to SCF (Stem Cell Factor) and galectin-1, in which the dual-targeting antibody comprises a light-chain variable region comprising light-chain CDR1 represented by the amino acid sequence represented by SEQ ID NO: 1, light-chain CDR2 represented by the amino acid sequence represented by SEQ ID NO: 2, and light-chain CDR3 represented by the amino acid sequence represented by SEQ ID NO: 3; and a heavy-chain variable region comprising heavy-chain CDR1 represented by the amino acid sequence represented by SEQ ID NO: 4, heavy-chain CDR2 represented by the amino acid sequence represented by SEQ ID NO: 5, and heavy-chain CDR3 represented by the amino acid sequence represented by SEQ ID NO: 6.

Further, the present disclosure provides DNA encoding a dual-targeting antibody specifically binding to SCF (Stem Cell Factor) and galectin-1, in which the DNA comprises: DNA encoding a light-chain variable region comprising nucleotide sequences represented by SEQ ID NO: 10, SEQ ID NO: 11 and SEQ ID NO: 12 respectively encoding a light-chain CDR1 represented by SEQ ID NO: 1, a light-chain CDR2 represented by SEQ ID NO: 2, and a light-chain CDR3 represented by SEQ ID NO: 3; and DNA encoding a heavy-chain variable region comprising nucleotide sequences represented by SEQ ID NO: 13, SEQ ID NO: 14 and SEQ ID NO: 15 respectively encoding a heavy-chain CDR1 represented by SEQ ID NO: 4, a heavy-chain CDR2 represented by SEQ ID NO: 5, and a heavy-chain CDR3 represented by SEQ ID NO: 6.

Further, the present disclosure provides a vector containing the DNA and provides a cell transformed with the vector.

Further, the present disclosure provides a pharmaceutical composition for prevention or treatment of angiogenesis-related diseases, the composition comprising the dual-targeting antibodies that specifically bind to the SCF and galectin-1.

Further, the present disclosure provides a method for preventing or treating angiogenesis-related disease, the method comprising administering a dual-targeting antibody that specifically binds the SCF and galectin-1 to a subject in need thereof.

Further, the present disclosure provides a composition for simultaneous detection of the SCF and the galectin-1, the composition comprising dual-targeting antibodies that specifically bind to the SCF and the galectin-1.

Advantageous Effects

The present disclosure may provide a human monoclonal antibody-derived dual-targeting antibody that may neutralize both the SCF and galectin-1 involved in angiogenesis to effectively inhibit angiogenesis. Further, the present disclosure provides a pharmaceutical composition for prevention or treatment of angiogenesis-related diseases, the composition containing the antibody. The dual-targeting antibodies according to the present disclosure simultaneously neutralize the two targets involved in neovascularization, thereby effectively preventing or treating the angiogenesis-related diseases causing bleeding due to the abnormal angiogenesis leading to change of blood vessels and increase in their permeability.

BRIEF DESCRIPTION OF THE DRAWINGS

FIG. 5 shows a nucleotide sequence, an amino acid sequence and a CDR region of a 3C4 antibody light-chain region.

FIG. 6 shows a nucleotide sequence, an amino acid sequence and a CDR region of a 3C4 antibody heavy-chain region.

DETAILED DESCRIPTION OF THE INVENTION

Figure 1:
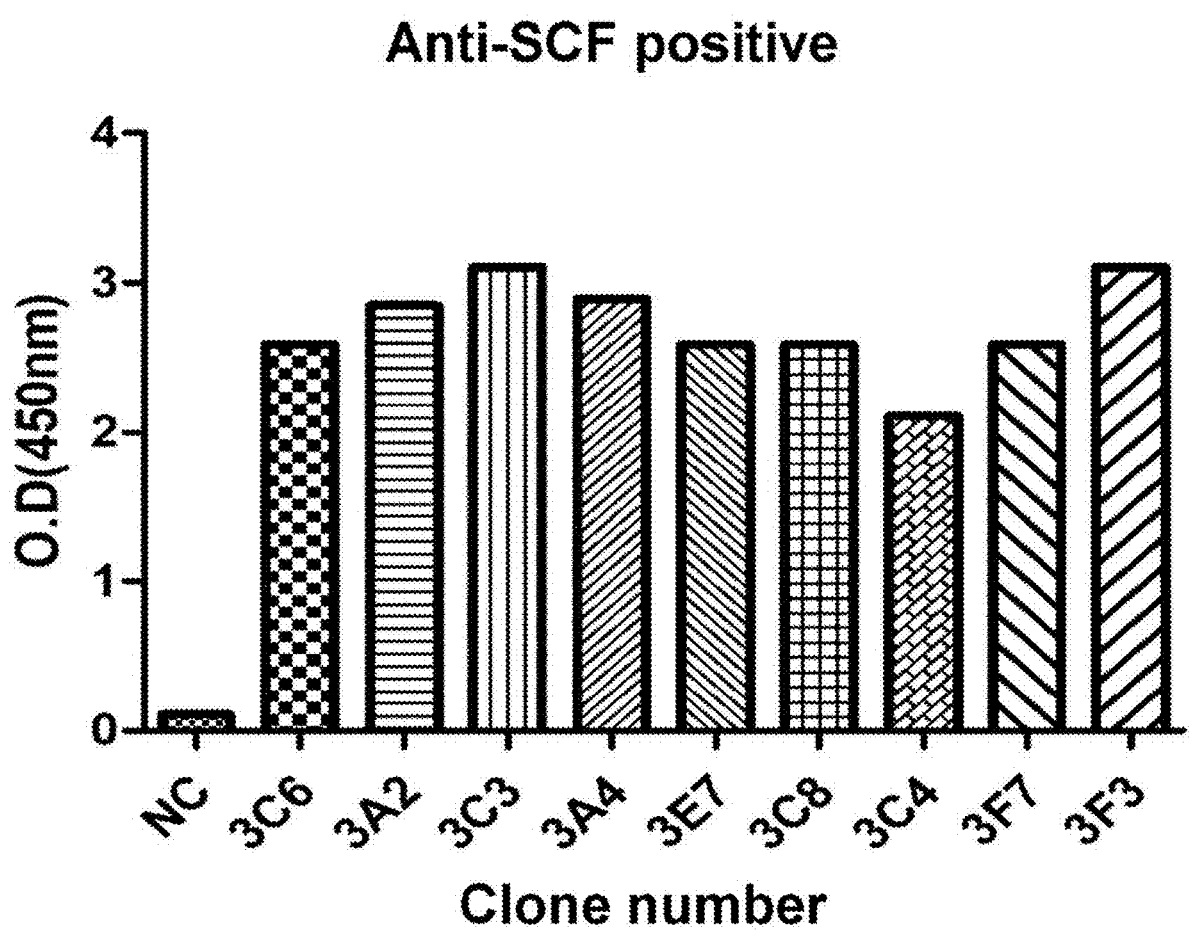
FIG. 1 shows a total of nine monoclonal antibodies 3C6, 3A2, 3C3, 3A4, 3E7, 3C8, 3C4, 3F7 and 3F3 selected by enzyme immunoassay.

Hereinafter, the present disclosure will be described in detail.

Terms not otherwise defined herein have a meaning commonly used in the technical field to which the present disclosure belongs.

The present inventors produced, for the first time, dual-targeting antibodies that inhibit angiogenesis in angiogenesis-related diseases to effectively prevent or treat the disease.

Since the dual-targeting antibody may suppress or amplify two signals at the same time, this may be more effective than suppressing/amplifying one signal. Since the dual-targeting antibody may suppress or amplify two signals at the same time, a low dose administration may be realized, compared to a case where each of the two signals is treated with each of different signal inhibitors. Thus, there is an advantage of suppressing/amplifying the two signals at the same time and space.

In the present disclosure, the dual-targeting antibody may be a 'polyclonal' or 'monoclonal' antibody. In one example, a monoclonal antibody is more preferred. The monoclonal antibody refers to an antibody obtained from a substantially homogeneous population of antibodies. That is, the individual antibodies that constitute this population are identical with each other except for possible naturally occurring mutations that may be present in a small amount. Monoclonal antibodies are highly specific to a single antigenic region. Moreover, in contrast to polyclonal antibodies that contain different antibodies to different epitopes, the monoclonal antibodies are specific to a single epitope on the antigen. "Monoclonal" should not be construed as requiring the production of antibodies using any specific method. For example, monoclonal antibodies in accordance with the present disclosure are produced by the hybridoma method described in an article [Kohler et al., Nature, 256: 495 (1975)], or by a recombinant DNA method [see U.S. Pat. No. 4,816,567]. Further, monoclonal antibodies may be isolated from phage antibody libraries using a scheme as described, for example, in an article [Clackson et al., Nature, 352: 624-628 (1991); Marks et al., J. Mol. Biol., 222: 581-597 (1991)].

In one aspect, the present disclosure provides a dual-targeting antibody specifically binding to SCF (Stem Cell Factor) and galectin-1, in which the dual-targeting antibody comprises: a light-chain variable region comprising a light-chain CDR1 represented by an amino acid sequence represented by SEQ ID NO: 1, a light-chain CDR2 represented by an amino acid sequence represented by SEQ ID NO: 2, and a light-chain CDR3 represented by an amino acid sequence represented by SEQ ID NO: 3; and a heavy-chain variable region comprising a heavy-chain CDR1 represented by an amino acid sequence represented by SEQ ID NO: 4, a heavy-chain CDR2 represented by an amino acid sequence represented by SEQ ID NO: 5, and a heavy-chain CDR3 represented by an amino acid sequence represented by SEQ ID NO: 6.

As used herein, the term "antibody" comprises not only a complete antibody form but also an antigen-binding fragment of an antibody molecule.

The complete antibody has two full-length light-chains and two full-length heavy-chains, in which each light-chain is linked to each heavy-chain via a disulfide bond. The heavy-chain invariable region has gamma (γ), mu (μ), alpha (α), delta (δ), and epsilon (δ) types. The heavy-chain invariable region has, as subclasses, gamma 1 (γ1), gamma 2 (γ2), and gamma 3 (γ3), gamma 4 (γ4), alpha 1 (α1), and alpha 2 (α2). The light-chain invariable region has kappa (κ) and lambda (λ) types (Cellular and Molecular Immunology, Wonsiewicz, M J, Ed., Chapter 45, pp. 41-50, WB Saunders Co. Philadelphia, Pa. (1991); Nisonoff, A., Introduction to Molecular Immunology, 2nd Ed., Chapter 4, pp. 45-65, sinauer Associates, Inc., Sunderland, Mass. (1984)).

As used herein, the term "antigen-binding fragment" refers to a fragment having an antigen-binding function and comprises Fab, F(ab'), F(ab')$_2$, Fv and the like. Fab of the antibody-binding fragment is composed of variable regions of a light-chain and a heavy-chain, an invariable region of a light-chain and a first invariable region ($C_{H1}$) of a heavy-chain and has one antigen-binding site. Fab' differs from Fab in that the former has a hinge region containing one or more cysteine residues in a C-terminal of the heavy-chain $C_{H1}$ domain. F(ab')$_2$ antibodies are produced when cysteine residues in the hinge region of Fab' form the disulfide bond. Fv is the smallest antibody moiety with only heavy-chain and light-chain variable regions. In the dual-chain Fv, the heavy-chain variable region and the light-chain variable region are connected to each other via a non-covalent bond. In a single-chain Fv, generally, the heavy-chain variable region and the light-chain variable region are connected to each other via a covalent bond through a peptide linker or are directly connected to each other at the C-terminal. Each of the dual-chain Fv and the single-chain Fv may form a dimer-like structure. These antibody fragments may be obtained using protease (for example, the restriction of the entire antibody using papain may yield an Fab, and the restriction of the entire antibody using the pepsin may yield an F(ab')$_2$ fragment), or may be produced by genetic recombination techniques.

In the present disclosure, the antibody is either the Fab form or the complete antibody form. Further, the heavy-chain invariable region may be selected from any one isotype of gamma (γ), mu (μ), alpha (α), delta (δ) or epsilon (ε). The light-chain invariable region may have either kappa or lambda type. According to one embodiment of the present disclosure, the light-chain invariable region may have a kappa type.

As used herein, the term "heavy-chain" refers to both of a full-length heavy-chain and fragments thereof, the full-length heavy-chain comprising the variable region domain $V_H$ comprising an amino acid sequence having sufficient variable region sequence to achieve specificity to the antigen, and three invariable region domains $C_{H1}$, $C_{H2}$ and $C_{H3}$. Further, the term "light-chain" herein refers to a full-length light-chain and fragments thereof, the full-length light-chain comprising the variable region domain $V_L$ comprising an amino acid sequence having sufficient variable region sequence to achieve specificity to the antigen, and an invariable region domain $C_L$.

As used herein, the term "CDR (complementarity determining region)" refers to the amino acid sequence of an immunoglobulin heavy-chain and light-chain hypervariable region (Kabat et al., Sequences of Proteins of Immunological Interest, 4th Ed., U.S. Department of Health and Human Services, National Institutes of Health (1987)). Each of the heavy-chain and light-chain comprises three CDRs (heavy-chains ($CDR_{H1}$, $CDR_{H2}$ and $CDR_{H3}$) and light-chains ($CDR_{L1}$, $CDR_{L2}$ and $CDR_{L3}$)). CDRs are annular regions that are involved in antigen recognition and provide important contact residues for the binding of the antibody to an antigen or epitope. Thus, the change of the sequence of the annular region determines the specificity of the antibody to the antigen.

In the present disclosure, the term "framework region (FR)" refers to a component that constitutes a variable region of an antibody and means a region positioned between the CDRs for supporting a ring structure of the CDR.

In the present disclosure, "dual-targeting antibodies" that specifically bind to SCF and galectin-1 may be used interchangeably with "anti-SCF antibody" or "dual-targeting antibody".

In the present disclosure, the antibody may comprise a light-chain variable region represented by the amino acid sequence represented by SEQ ID NO: 7 or a heavy-chain variable region represented by the amino acid sequence represented by SEQ ID NO: 8.

Further, according to the present disclosure, the antibody may be characterized as being represented by the amino acid sequence represented by SEQ ID NO: 9.

The dual-targeting antibody or antigen-binding fragment thereof according to the present disclosure may comprise variants of amino acid sequences listed in the attached sequence list as long as they specifically recognize the SCF and the galectin-1. For example, the amino acid sequence of the antibody may be altered to improve its binding affinity and/or other biological properties. Such modifications include, for example, deletions, insertions and/or substitutions of amino acid sequence residues of the antibody.

Such amino acid variation is based on the relative similarity of amino acid side chain substituents, such as hydrophobicity, hydrophilicity, charge, size, and the like. Analysis of the size, shape and type of amino acid side chain substituents may indicate that all of arginine, lysine and histidine are positively charged residues; alanine, glycine and serine have similar sizes; and phenylalanine, tryptophan and tyrosine have a similar shape. Thus, based on these considerations, arginine, lysine and histidine; alanine, glycine and serine; and phenylalanine, tryptophan, and tyrosine are biologically functional equivalents.

In introducing the mutations, the hydropathic index of amino acids may be considered. Each amino acid is assigned a hydrophobicity index depending on its hydrophobicity and charge: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydrophobicity index of the amino acid is very important in achieving the interactive biological function of proteins. It is known that substitution with amino acids having a similar hydrophobicity index may achieve similar biological activity. When introducing mutations with reference to the hydrophobicity index, substitutions are made between amino acids which exhibit the hydrophobicity index difference therebetween preferably within ±2, more preferably within ±1, even more preferably within ±0.5.

In one example, it is well known that substitutions between amino acids with similar hydrophilicity values result in proteins with equivalent biological activities. The following hydrophilicity values are assigned to the amino acid residues: arginine (+3.0); lysine (+3.0); asphaltate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

When introducing mutations with reference to hydrophilicity values, substitutions are made between amino acids which exhibit a hydrophilicity value difference therebetween preferably within ±2, more preferably within ±1, even more preferably within ±0.5.

Further, amino acid exchange in proteins that do not alter the activity of the molecule as a whole is known in the art (H. Neurath, R. L. Hill, The Proteins, Academic Press, New York, 1979). The most commonly occurring exchanges are the exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

Further, in the present disclosure, dual-targeting antibodies that specifically bind to SCF and galectin-1 according to the present disclosure may be characterized by including a human IgG1-derived invariable region. According to one embodiment of the present disclosure, the present disclosure provides a 3C4 antibody as a dual-targeting antibody including a human IgG1-derived invariable region, in addition to the light-chain variable region and heavy-chain variable region as described above.

The dual-targeting antibody according to the present disclosure is preferably a "humanized antibody". The humanized antibody refers to an antibody composed of an amino acid sequence derived in part or in whole from a human antibody germline by altering a sequence of an antibody having a non-human complementarity determining region (CDR). More preferably, the antibody according to the present disclosure may be a "human antibody". In the present disclosure, the term "human antibody" broadly refers to an antibody including variable regions (CDRs and FRs) derived from human immunoglobulins. The human antibody refers to, in a narrow sense, antibodies including variable and invariable (constant) regions derived from human immunoglobulins. The human antibody may be not only a whole antibody form but also may contain functional fragments of antibody molecules. Human antibodies may be produced using a variety of techniques known in the art.

Because all of components of the human antibody are derived from humans, the chance of an immunization reaction is less likely in the human antibody compared to the existing humanized or mouse antibodies. Thus, when the human antibody is administered to humans, there is an advantage that an unwanted immune response does not occur. Therefore, the human antibody may be very useful as a therapeutic antibody for humans.

For purposes of the present disclosure, the human antibody may be considered as a dual-targeting antibody that specifically binds to the SCF and galectin-1 in accordance with the present disclosure. The human antibody may specifically bind to the SCF and the galectin-1 to significantly inhibit neovascular expression induced by the SCF and galectin-1. However, the present disclosure is not particularly limited thereto.

In addition, the human antibody is not particularly limited thereto but may be glycosylated and/or PEGylated in order to enhance a retention time thereof in the body when the antibody is administered thereto.

The term "glycosylation" according to the present disclosure refers to a processing method for translating glycosyl groups to proteins. The glycosylation is carried out such that glycosyl groups coupled to serine, threonine, asparagine or hydroxylysine residues of the target protein via glycosyl transferase. The glycated proteins may not only be used as constituents of biological tissues but also play an important role in cell recognition at the cell surface. Thus, the present disclosure may enhance the effects of human antibodies by altering the glycosylation of the human antibody or the pattern of the glycosylation.

The term "PEGlation" according to the present disclosure refers to a processing method that improves the in-blood retention time of the human antibody by introducing polyethylene glycol into the human antibody (Anna M. Wu, et al., Nature Biotechnology, 23 (9): 1137-1146, 2005; David Schrama, et al., Drug Discovery, 5: 147-159, 2006; Alain Beck, et al., Immunology, 10: 345-352, 2010). Specifically, PEGlation of the polymer nanoparticles using polyethylene glycol may allow the hydrophilicity of the surface of the nanoparticles to be increased. Thus, rapid degradation of the antibody in the body may be prevented via the so-called stealth effect, which prevents recognition from immune functions including macrophage in the human body to prey and digest pathogens, waste products and foreign incoming substances. Therefore, the in-blood retention time of the antibody may be improved by the PEGlation. The PEGlation used in the present disclosure may be carried out using a method of forming an amide group by combining a carboxyl group of hyaluronic acid with an amine group of polyethylene glycol. However, the present disclosure is not limited thereto, and the PEGlation may be performed by various methods. In this connection, the polyethylene glycol to be used is not particularly limited, but preferably has a molecular weight between 100 to 1,000, and having a linear or branched structure.

Regarding the glycosylation and/or PEGlation, various glycosylation and/or PEGlation patterns may be modified by methods known in the art as long as the modified patterns retain the function of the antibody according to the present disclosure. The human antibodies according to the present disclosure include all mutated human antibodies with the various modified glycosylation and/or PEGlation patterns.

Further, the present disclosure provides DNA encoding a dual-targeting antibody specifically binding to SCF (Stem Cell Factor) and galectin-1, in which the DNA comprises: DNA encoding a light-chain variable region comprising nucleotide sequences represented by SEQ ID NO: 10, SEQ ID NO: 11 and SEQ ID NO: 12 respectively encoding a light-chain CDR1 represented by SEQ ID NO: 1, a light-chain CDR2 represented by SEQ ID NO: 2, and a light-chain CDR3 represented by SEQ ID NO: 3; and DNA encoding a heavy-chain variable region comprising nucleotide sequences represented by SEQ ID NO: 13, SEQ ID NO: 14 and SEQ ID NO: 15 respectively encoding a heavy-chain CDR1 represented by SEQ ID NO: 4, a heavy-chain CDR2 represented by SEQ ID NO: 5, and a heavy-chain CDR3 represented by SEQ ID NO: 6.

According to the present disclosure, the DNA encoding the light-chain variable region may be characterized as being represented by SEQ ID NO: 16.

Further, according to the present disclosure, the DNA encoding the heavy-chain variable region may be characterized as being represented by SEQ ID NO: 17.

Further, according to the present disclosure, the DNA encoding the dual-targeting antibody may be characterized as being represented by SEQ ID NO: 18.

When considering the variations with biologically equivalent activity as described above, the antibody according to the present disclosure or nucleic acid molecule encoding the antibody is to be construed to comprise a sequence that exhibits substantial identity to the sequence listed in the sequence listing. When the sequence according to the present disclosure is aligned with any other sequence as closely as possible, and then the aligned sequences are analyzed using algorithms commonly used in the art, the above substantial identity may mean at least 61% homology, more preferably 70% homology, even more preferably 80% homology, most preferably 90% homology. The alignment methods for sequence comparison are known in the art.

As used herein, the term "nucleic acid molecule" is meant to encompass DNA (gDNA and cDNA) and RNA molecules inclusively. The nucleotides, which are the basic structural units of nucleic acid molecules include not only natural nucleotides but also analogues in which sugar or base regions are modified. The nucleic acid molecular sequence encoding the heavy-chain variable region and light-chain variable region according to the present disclosure may be modified. The modification includes addition, deletion or non-conservative substitutions or conservative substitutions of nucleotides.

The nucleic acid molecule according to the present disclosure encoding the dual-targeting antibody according to the present disclosure is to be interpreted to include a nucleotide sequence showing substantial identity to the nucleotide sequence as described above. When the sequence according to the present disclosure is aligned with any other sequence as closely as possible, and then the aligned sequences are analyzed using algorithms commonly used in the art, the above substantial identity may mean a sequence that exhibits 80%, 90% or 95% homology.

Further, the present disclosure provides a vector containing the DNA and provides a cell transformed with the vector.

As used herein, the term "vector" refers to means for expressing a gene of interest from a host cell and may include a plasmid vector; cosmid vector; and viral vectors such as bacteriophage vectors, adenovirus vectors, retrovirus vectors, and adeno-associated virus vectors, and the like.

The DNA encoding the dual-targeting antibody in the vector according to the present disclosure may be operatively linked with the promoter.

As used herein, the term "operably linked" means a functional binding between a nucleic acid expression control sequence (e.g., a promoter or array of transcriptional regulator binding sites) and another nucleic acid sequence. Thus, the regulatory sequence regulates the transcription and/or translation of the another nucleic acid sequence.

A recombinant vector system according to the present disclosure may be constructed via a variety of methods known in the art and may typically be constructed as a vector for cloning or a vector for expression. Further, according to the present disclosure, a vector may be constructed using prokaryotic or eukaryotic cells as hosts.

In one example, the expression vector according to the present disclosure may include antibiotic resistance genes commonly used in the art as a selection marker. The antibiotic resistance gene may be one or more selected from ampicillin, gentamicin, carbenicillin, chloramphenicol, streptomycin, kanamycin, geneticin, neomycin and tetracycline.

Further, in the present disclosure, the cell may be a bacterial or animal cell.

The cell transformed with the vector is a host cell capable of stably and continuously cloning and expressing the vector according to the present disclosure, and any host cell known in the art may be used. For example, eukaryotic host cells suitable for the vector include monkey kidney cells 7 (COST), NSO cells, SP2/0, Chinese hamster ovary (CHO) cells, W138, young hamster kidneys (BHK: baby hamster kidney) cells, MDCK, myeloma cell line, HuT 78 cells and HEK-293 cells. The host cell may be preferably CHO cells, but is not limited thereto.

Further, the present disclosure provides a pharmaceutical composition for the prevention or treatment of angiogenesis-related diseases, the composition comprising dual-targeting antibodies that specifically bind to SCF and galectin-1 according to the present disclosure.

Since the pharmaceutical composition according to the present disclosure contains the dual-targeting antibody or antigen-binding fragment thereof according to the present disclosure described above as an active ingredient, the descriptions common between the dual-targeting antibody and antigen-binding fragment thereof are omitted in order to avoid excessive complexity of the present specification due to the repeated description.

According to the present disclosure, the angiogenesis-related disease refers to a disease resulting from the formation of blood vessels. Angiogenesis-related diseases according to the present disclosure include ocular vascular diseases, rheumatoid arthritis, psoriasis, cancer, tumor metastasis, delayed wound healing, chronic inflammation, atherosclerosis, stenosis, vascular malformation, vascular access dysfunction in patients with hemodialysis, transplant arteriopathy, vasculitis, DiGeorge syndrome, hereditary hemorrhagic telangiectasia, cavernous malformation, keloid scar, pyogenic granuloma, blister, kaposi's sarcoma, proliferative vitreoretinopathy, primary pulmonary hypertension, asthma, nasal polyps, inflammatory bowel disease, periodontal disease, ascites, peritoneal adhesion, endometriosis, uterine bleeding, ovarian cyst, ovarian hyperstimulation syndrome, synovitis, osteomyelitis, osteophyma, sepsis, infectious disease and autoimmune disease, and the like. Preferably, the angiogenesis-related disease may be the ocular vascular disease, but is not necessarily limited thereto.

Further, according to the present disclosure, the ocular vascular disease includes at least one selected from a group consisting of macular degeneration, age-related macular degeneration, diabetic retinopathy, choroidal neovascularization, glaucoma retinitis pigmentosa, retinopathy of prematurity, glaucoma, corneal dystrophy, and retinoschisis. Preferably, the ocular vascular disease may be the age-related macular degeneration or diabetic retinopathy.

As demonstrated in the following examples, the dual-targeting antibody according to the present disclosure may inhibit the neovascularization of vascular endothelial cells, and thus may be effective in preventing or treating angiogenesis-related disease.

Pharmaceutically acceptable carriers included in the pharmaceutical composition according to the present disclosure are those commonly used in the formulation and may comprise lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil and the like, but may not be limited thereto. The pharmaceutical composition according to the present disclosure may further comprise lubricants, wetting agents, sweeteners, flavors, emulsifiers, suspending agents, preservatives, etc. in addition to the components. Suitable pharmaceutically acceptable carriers and formulations are described in detail in Remington's Pharmaceutical Sciences (19th ed., 1995).

The pharmaceutical composition according to the present disclosure may be administered parenterally, for example, in an intravenous, subcutaneous, intramuscular, intraperitoneal, topical, intranasal, pulmonary and rectal manner.

The appropriate dosage of the pharmaceutical composition according to the present disclosure varies by factors such as the formulation method, mode of administration, patient age, weight, sex, morbidity, food, time of administration, route of administration, rate of excretion and response sensitivity. Usually, an experienced physician may easily determine and prescribe a dosage effective for the desired treatment or prophylaxis. For example, the daily dosage of the pharmaceutical composition according to the present disclosure may be 0.0001 to 100 mg/kg. As used herein, the term "pharmaceutically effective amount" means an amount sufficient to prevent or treat the angiogenesis-related disease.

The pharmaceutical composition according to the present disclosure may be formulated using pharmaceutically acceptable carriers and/or excipients according to the method which may be easily carried out by those skilled in the art and thus may be produced in a unit dose form or may be incorporated into a multi-dose container. The formulation may be in the form of solutions in oils or aqueous media, suspensions or emulsions or in the form of extracts, powders, suppositories, granules, tablets or capsules, and may further comprise a dispersant or stabilizer.

Further, the pharmaceutical composition according to the present disclosure may be used in combination with or may be mixed with other therapeutic agents targeting VEGF. This may result in synergism such as more effective suppression of abnormal neovascularization. The therapeutic agent that targets the VEGF may preferably be, but not limited to, eylea (Aaflibercept) or Lucentis (Ranibizumab).

Further, the present disclosure may provide a method for preventing or treating angiogenesis-related disease, the method comprising administering a dual-targeting antibody that specifically binds to SCF and galectin-1 according to the present disclosure to a subject in need thereof.

The subject is preferably a mammal, including humans and may be patients in need of treatment for angiogenesis-related disease. The patient may include patients undergoing angiogenesis-related disease treatment, patients who have been subjected to angiogenesis-related disease treatment, and patients in need of treatment of angiogenesis-related disease, and also patients who have undergone surgical operations to treat angiogenesis-related disease. Administering the pharmaceutical composition according to the present disclosure to an individual may allow the angiogenesis-related disease to be alleviated or treated.

As used herein, the term "alleviation" refers to any action in which angiogenesis-related disease is reduced via or benefits from administration of the pharmaceutical composition in accordance with the present disclosure. The pharmaceutical composition according to the present disclosure is administered in a pharmaceutically effective amount.

As used herein, the term "administration" refers to the introduction of a pharmaceutical composition according to the present disclosure to a subject using any suitable method. Routes of administration may include various oral or parenteral routes as long as the composition reaches the desired tissue through the routes.

In addition, the pharmaceutical composition for the prevention or treatment of angiogenesis-related diseases comprising the dual-targeting antibody that specifically binds to the SCF and galectin-1 according to the present disclosure may be administered simultaneously/sequentially in combination with other existing drugs for the treatment of angiogenesis-related diseases or with existing treatment methods thereof. Such administration may be single or multiple administration. It is important to administer an amount that will achieve the maximum effect with a minimum amount without side effects while taking into account all the factors. The amount may be easily determined by those skilled in the art.

Further, the present disclosure may provide a neovascularization inhibition method comprising administering a dual-targeting antibody that specifically binds to SCF and galectin-1 according to the present disclosure to a subject in need thereof.

Specifically, the method may simultaneously neutralize not only SCF but also galectin-1 to inhibit the neovascularization induced by SCF and galectin-1. The method may inhibit c-kit phosphorylation induced by SCF and may inhibit phosphorylation of AKT and ERK as downstream signaling pathways, thereby effectively preventing the tube formation of vascular endothelial cells induced by the SCF and galectin-1.

Further, the present disclosure provides a composition for the simultaneous detection of SCF and galectin-1, the composition comprising a dual-targeting antibody that specifically binds to SCF and galectin-1 according to the present disclosure, and provides a kit comprising the composition for the simultaneous detection of SCF and galectin-1.

The composition and the kit for detection according to the present disclosure comprise the dual-targeting antibody or antigen-binding fragment thereof according to the present disclosure. The composition and the kit may have specific binding to the SCF and the galectin-1 to allow simultaneous detection thereof.

Since the composition and the kit for detection according to the present disclosure comprise the antibody, the composition and the kit may be basically prepared suitable for various immunoassays or immunostaining. The immunoassay or immunostaining may include radioimmunoassay, radioimmunoprecipitation, immunoprecipitation, enzyme-linked immunosorbent assay (ELISA), capture-ELISA, inhibition or competition assay, sandwich assay, flow cytometry, immunofluorescence staining and immunoaffinity purification but may not be limited thereto.

Samples that may be applied to the detection composition and kit according to the present disclosure include, but are not limited to, cells, tissues or tissue-derived extracts, lysates or purified products, blood, plasma, serum, lymph or ascites.

Hereinafter, the present disclosure will be described in detail with reference to a preferred example. However, the following example is only to illustrate the present disclosure, but the content according to the present disclosure is not limited to the example.

Example 1

Construction of Cell Line for Producing Dual-Targeting Antibody Targeting SCF and Galectin-1

1-1. Immunization of Mice

50 μg of recombinant Stem Cell Factor (SCF) protein (cat #7466-SC) purchased from R & D systems was mixed with a complete Freund's Adjuvant (Sigma, USA) at an equal volume ratio to produce an emulsion (per one mouse). The emulsion was injected intraperitoneally in four humanized NSG mice as produced by injection of 7 week old female human CD34+ cells. Thereafter, 50 μg of the antigen was injected into each mouse at a total volume of 500 μl to induce antibody production. One week and two weeks later, a mixed emulsion between an incomplete Freund's adjuvant (Sigma, USA) and an antigen was further injected intraperitoneally to the mouse.

1-2. Identification and Screening of Antibody-Producing Cells

Blood was collected from the eye of the immunized mice via the above method and was placed in a 1.5 ml microcentrifuge tube and was centrifuged at 13,000 rpm for 10 minutes. Serum was separated therefrom and was stored at −20° C. until the experiment was performed to identify antibody production. Enzyme-immunoassay using antigenic protein was performed to identify whether the antibody was produced, and then, three days before cell fusion, a mixed emulsion between the incomplete Freund's adjuvant (Sigma, USA) and the antigen was injected into the abdominal cavity of the mouse.

1-3. Hybridoma Producing

After identifying the antibody production, mice were sacrificed to isolate splenocyte. Then, hybridomas were produced by fusion of the splenocyte with myeloma cells P3X63Ag8.653 (ATCC CRL-1580).

First, P3X63Ag8.653 cells of mice were cultured in culture plates using RPMI1640 medium supplemented with 10% fetal bovine serum. To perform cell fusion, P3X63Ag8.653 cells were washed twice with serum-free RPMI1640 medium (Hyclone, USA) and a cell concentration thereof was adjusted to $1 \times 10^7$. Mice were sacrificed by cervical dislocation and spleens were collected therefrom, then and were placed in a mesh container (Sigma, USA) to separate cells therefrom. After producing a suspension of splenocytes, the suspension was washed by centrifugation. A splenocyte solution was exposed to Tris-NH$_4$Cl (Tris 20.6 g/L, NH4Cl 8.3 g/L) to lyse red blood cells. Completely separated antibody-producing cells were centrifuged at 400× g for 5 minutes, and were washed twice in serum-free medium and were resuspended in 10 ml medium. Lymphocytes were counted using a hemocytometer and then $1 \times 10^8$ lymphocytes were mixed with $1 \times 10$ P3X63Ag 8.653 cells (10:1) in serum-free medium. Centrifugation was carried out at 400×g for 5 minutes. Thereafter, 1 ml of a 50% (M/V) polyethylene glycol 1500 (Sigma, USA) solution heated to 37° C. was slowly added thereto and both were mixed with each other for 1 minute.

The fusion mixture solution as produced above was diluted with serum-free RPMI1640 and centrifuged at 400×g for 3 minutes. Cells were suspended in 35 ml RPMI1640 selection medium supplemented with 20% fetal bovine serum and HAT (100 μM hypoxanthine, 0.4 μM aminopterin, 16 μM thymidine). 100 μl of the suspension was loaded in 96-well plates coated with feeder cells (macrophages isolated from the abdominal cavity using RPMI1640) one day before and the cells were incubated therein at 37° C., 5% CO$_2$. After 5 days, HAT medium was replaced every 2 to 3 days and the cells were incubated for 14 days. After 14 days, the RPMI1640 medium supplemented with 20% fetal bovine serum and HT (medium in which 0.4 μM aminopterin is removed from HAT) was replaced and then the cells were second cultured. The lymphocytes isolated from the SCF-immunized lymph nodes were fused with myeloma cells to obtain supernatants of hybridoma colonies which in turn were used for subsequent experiments.

1-4. Selection and Isolation of Antibody-Producing Fusion Cells

Supernatants of the hybridoma colonies produced in Example 1-3 were collected and subjected to enzyme immunoassay to identify the production of antibodies specific to the produced antigen. Culture solutions of fusion cells exhibiting an appropriate concentration of 4 or more times compared to that of the negative control group were selected and transferred to 24-well culture plates for culture. In addition, the cells were subjected to limiting dilution such that one cell per well was contained in a 96-well plate and were cultured and then the culture solution was collected. Thereafter, the SCF protein used as the antigen was coated on a 96-well plate at 0.1 μg per well, followed by enzyme immunoassay. As a result, fusion cells producing nine monoclonal antibodies (3C6, 3A2, 3C3, 3A4, 3E7, 3C8, 3C4, 3F7 and 3F3) were finally selected by measuring optical density (OD value) at 450 nm wavelength. This is shown in FIG. 1.

Example 2

Determination of SCF Neutralization Capacity of Dual-Targeting Antibody

After dispensing 300 μl of Matrigel (Corning, USA) into 12-well plates, Human Umbilical Vein Endothelial Cells (HUVECs) were mixed with SCF (50 ng/ml) or SCF (50 ng/ml)+anti-SCF antibody (10 μg/ml) and then the mixture was added to Matrigel to observe tube formation of HUVECs in vitro (n=10). The results are shown in FIG. 2.

Figure 2:
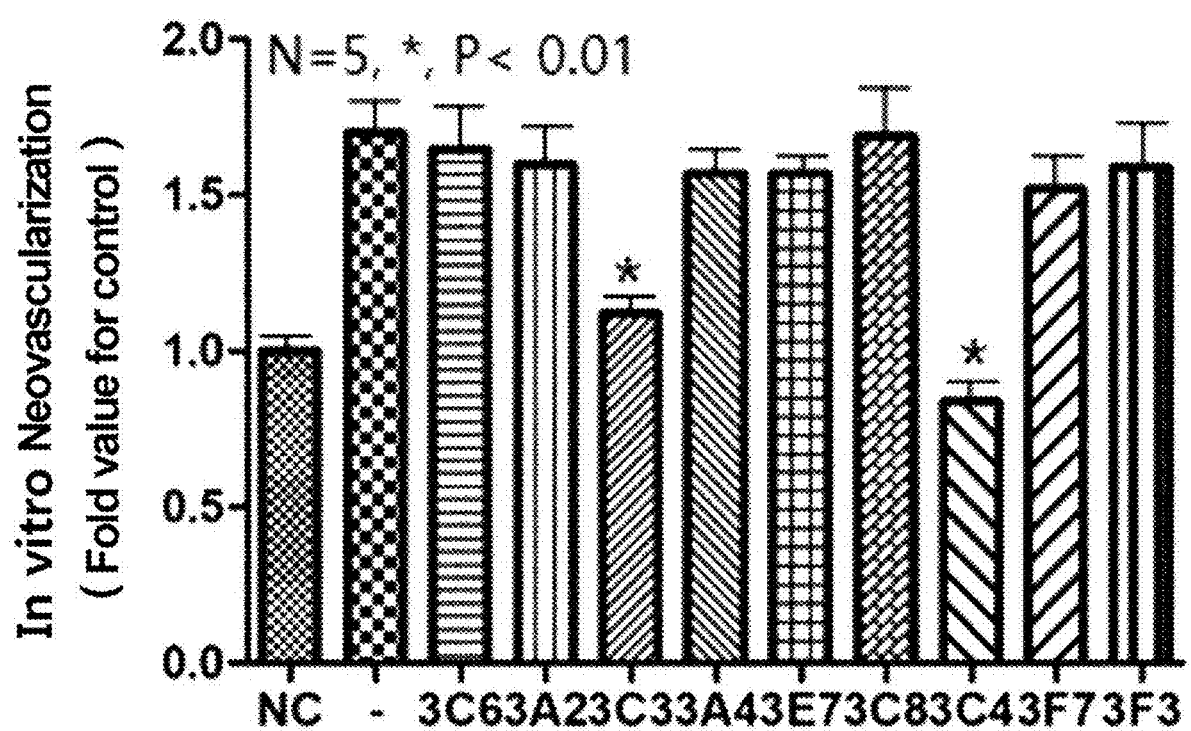
FIG. 2 shows an ability of each of a total of nine monoclonal antibodies according to the present disclosure to inhibit tube formation of HUVEC (vascular endothelial cells) when the vascular endothelial cells (HUVECs) are treated with the total of nine monoclonal antibodies.

As shown in FIG. 2, it was identified that 3C3 and 3C4 antibodies out of nine monoclonal antibodies effectively inhibit tube formation of HUVEC induced by SCF. The results identified that 3C3 and 3C4 antibodies according to the present disclosure could inhibit the neovascularization and may be used to prevent or treat angiogenesis-related diseases.

Example 3

Nucleotide Sequence Analysis of Igg Variable Regions

3-1. cDNA Synthesis from Fusion Cells

Total RNA was isolated from $5 \times 10^5$ fusion cell 3C4 clones obtained in Examples 1 and 2. Then, reverse transcription of the isolated RNA was performed using a random primer (bioneer, Korea) and reverse transcriptase.

3-2. PCR Amplification of Mouse IgG Variable Domain

Variable region-specific primers to the cDNA obtained by reverse transcription were used to amplify the light-chain and heavy-chain regions of the antibody. The primers used are shown in Table 1 below.

TABLE 1

The primers used

| Type | Sequence (5'-3') | SEQ ID NO: |
|---|---|---|
| Light-chain | CAGCTCCTGGGGCTGCTAATGCTCTGG (forward direction) | 19 |
| | CAGTTGCTAACTGTTCCGTGGATG (reverse direction) | 20 |
| Heavy-chain | ATGGARTTGGGGCTGWGCTGGGTTTT (forward direction) | 21 |
| | ACTTTTGAGAGCAGTTCCAGGAGC (reverse direction) | 22 |

Figure 3:
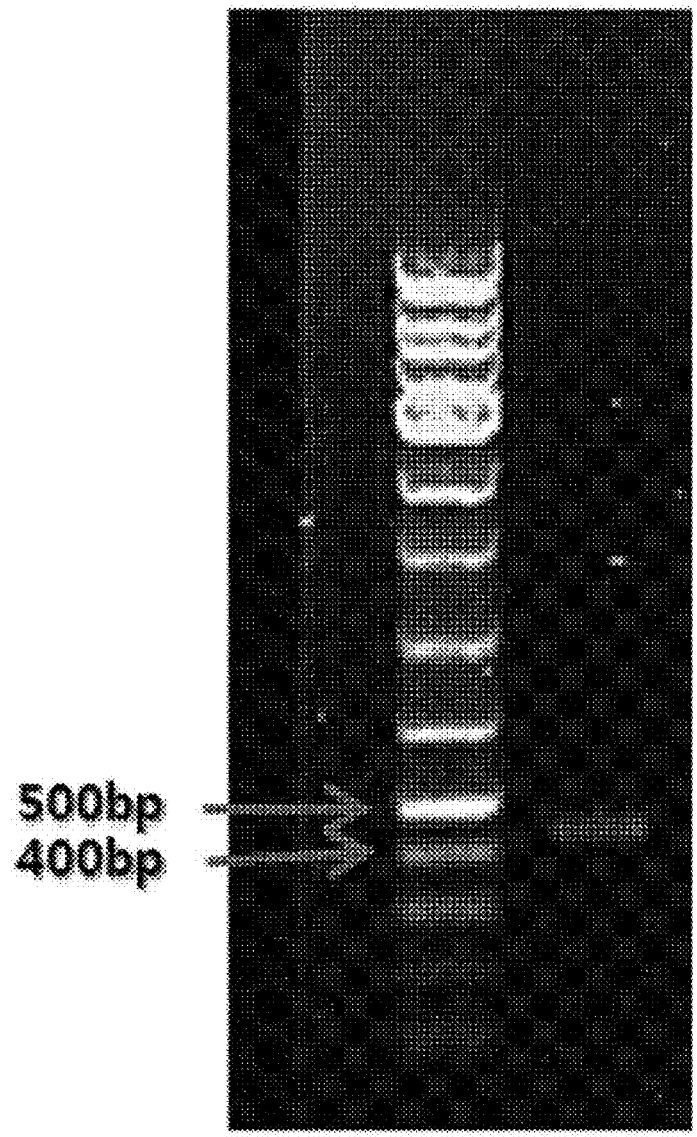
FIG. 3 shows results of electrophoresis of DNA of a light-chain domain of a 3C4 antibody variable region as amplified by PCR using 1% agarose gel.

First, kappa light-chain domains were amplified from cDNA using primers represented by SEQ ID NOs: 1 and 2. Amplified DNA was identified by agarose gel electrophoresis, the results are shown in FIG. 3. Further, the IgG1 heavy-chain domain was amplified from cDNA using primers represented by SEQ ID NOs: 3 and 4. Likewise, amplified DNA was identified by agarose gel electrophoresis and the results are shown in FIG. 4.

Figure 4:
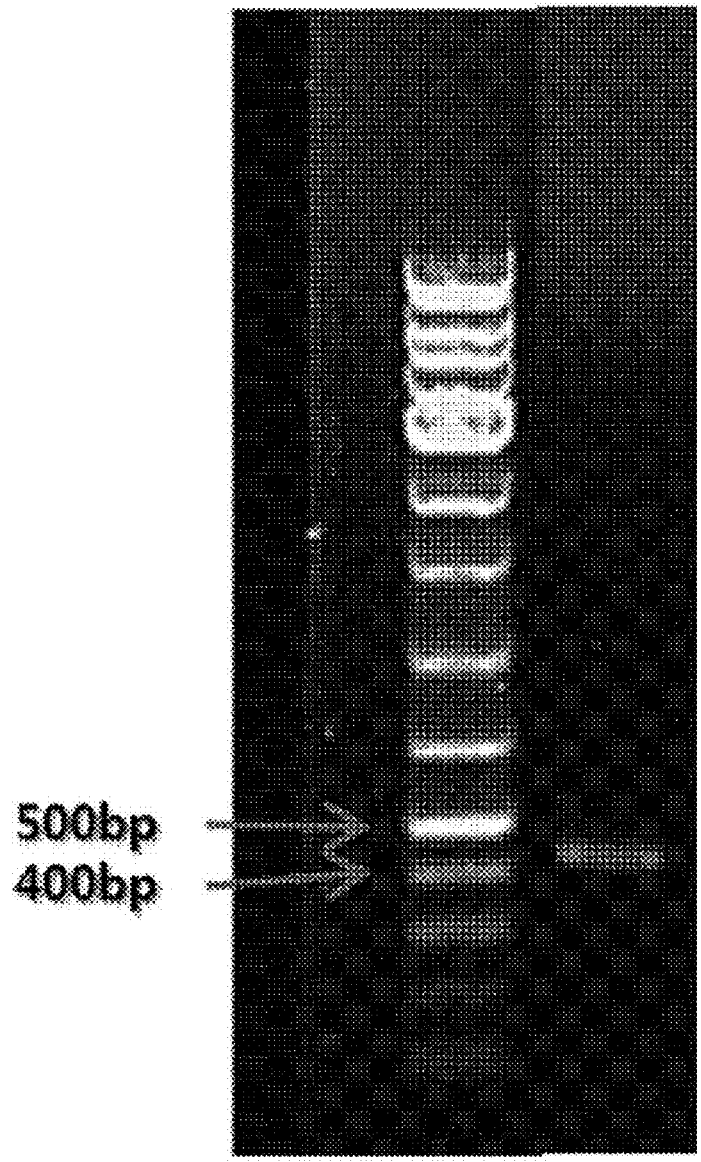
FIG. 4 shows results of electrophoresis of a heavy-chain domain of a 3C4 antibody variable region as amplified by PCR using 1% agarose gel.

As shown in FIG. 3 and FIG. 4, bands were found between the kappa light-chain domain (414 bp) and the heavy-chain domain (483 bp) to identify PCR products of expected sizes. No other PCR product was found in the other PCR used as a negative control.

Thereafter, the PCR product was developed on an agarose gel to cut a band. The agarose gel was dissolved at 60° C., and DNA was purified using a spin column (Qiagen). The purified DNA was cloned into a TOPO-TA vector (Invitrogen), and thus transformed into *E. coli* DH5a to obtain colonies which were cultured. Then, plasmids were extracted therefrom, and then PCR was performed again to obtain 4 plasmids. Then, nucleotide sequence analysis of the 3C4 antibody was performed. The sequence identified through the nucleotide sequence analysis is shown in Table 2. In one example, the sequence analysis revealed that the 3C3 clone had the same nucleotide sequence as the 3C4 clone. nucleotide sequence, amino acid sequence, and CDR region of 3C4 antibody are shown in FIG. 5 and FIG. 6.

As shown in FIG. 5, the light-chain of 3C4 includes CDR1 (SEQ ID NO: 1), CDR2 (SEQ ID NO: 2), and CDR3 (SEQ ID NO: 3) of the light-chain in the order of blue letters. As shown in FIG. 6, the heavy-chain of 3C4 includes CDR1 (SEQ ID NO: 4), CDR2 (SEQ ID NO: 5) and CDR3 (SEQ ID NO: 6) in the order of blue letters.

Further, the light-chain amino acid sequence of 3C4 is indicated as a SEQ ID NO: 7, the heavy-chain amino acid sequence thereof is indicated as a SEQ ID NO: 8, and the total amino acid sequence of 3C4 is indicated as SEQ ID NO: 9. The light-chain (SEQ ID NO: 16) and heavy-chain (SEQ ID NO: 17) nucleotide sequences of 3C4 are shown in Table 2, and the entire nucleotide sequences of 3C4 are indicated as SEQ ID NO: 18.

TABLE 2

The light-chain (SEQ ID NO: 16) and heavy-chain (SEQ ID NO: 17) nucleotide sequences of 3C4

| Type | Sequence (5'-3') | SEQ ID NO: |
|---|---|---|
| Light-chain | GAT GTT GTG ATG ACT CAG TCT CCA CTC TCC CTG CCC GTC ACC CTT GGA CAG CCG GCC TCC ATC TCC TGC AGG TCT AGT CAA ACC CTC GTA TAC AGT GAT GCA AAC ACC TAC TTG AAT TGG TTT CAG CAG AGG CCA GGC CAA TCT CCA AGG CGC CTA ATT TAT AAG GTT TCT AAC CGG GAC TCT GGG GTC CCA CAG AGA TTC AGC GGC AGT GGG TCA GGC ACT GAT TTC ACA CTG AAA ATC AGC AGG GTG GAG GCT GAG GAT GTT GGG GTT TAT TAC TGC ATG CAA GGT ACA CAC TGG CCT CTT TCG GCG GAG GGA CCA AGG TGG AGA TCA AAC | 16 |
| Heavy-chain | CAG GTG CAG CTG GTG GAG TCT GGG GGA GGC GTG GTC CAG CCT GGG AGG TCC CTG AGA CTC TCC TGT GTA GCG TCT GGA TTC ACC TTC AGT AGC TAT GGC ATG CAC TGG GTC CGC CAG GCT CCA GGC AAG GGG CTG GAC TGG GTG GCA GTT ATA TGG TAT GAT GGA AGT AAT AAC GAC TAT GCA GAC TCC GTG AAG GGC CGA TTC ACC ATC TCC AGA GAC AAT TCC AAG AAC ACA CTG TAT CTA CAA ATC AAC AGC CTG AGA GCC GAG GAC ACG GCT GTA TAT TAC TGT GCG AGA GGG CAA AAT TAC TAT GGT TTG GGG AGT TAT TTC TTT GAC TAC TGG GGC CAG GGA ACC CTG GTC ACC | 17 |

The bold and underlined portions are the Complementarity determining region (CDR) sequence and indicate CDR1, CDR2 and CDR3 sequences in this order.

Example 4

Cloning of Human Antibody

The variable domain of anti-SCF antibody 3C4 (hereinafter referred to as 3C4) obtained in Example 3 was grafted onto human Fc amino acid sequence and then cloned into pCHO vector (lifetechnology).

The light-chain variable domains were fused within the frame for the human kappa invariable region and the heavy-chain variable domains were fused within the frame for the human IgG1 invariable region. The leader peptide sequence for secretion of the full-length IgG1 antibody into the medium was added to both the genes, and the genes were synthesized and verified again by sequence analysis. Three clones were selected for expression testing in CHO cells. Glycerol stocks for three clones were produced and endotoxin-free plasmid DNA was produced for expression testing in CHO cells.

Example 5

Isolation and Purification of Antibody after Transfection into CHO Cells

The plasmid DNA obtained in Example 4 was transfected into CHO-S cells. One week before the transfection, CHO-S (Invitrogen, 10743-029) was transferred into a monolayer culture in DMEM supplemented serum. Cells were dispensed 1 day before transfection, and then, DNA-lipofectamine complexes were prepared for the transfection samples. The cells were incubated at 5% $CO_2$ and 37° C. in an incubator overnight. For one week, the cells were cultured in medium while the medium was added every 2 to 3 days. The culture solution was collected and was bound to Protein A/G agarose (company) and then was washed with PBS. Then, after elution with 0.1 M glycine (pH 2.8), the cells were neutralized with 1 M Tris-HCl (pH 8.0). After dialysis again with PBS, the cells were stored at −70° C. The results are shown in FIG. 7.

Figure 7:
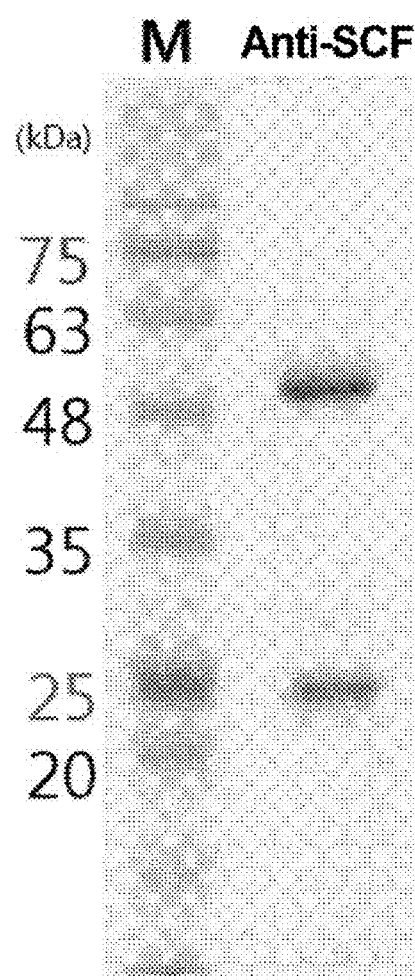
FIG. 7 shows results of SDS-PAGE analysis of separated and purified human 3C4 antibody expressed in animal cell lines.

As shown in FIG. 7, SDS-PAGE showed that heavy-chain band of about 50 kDa and light-chain band of about 25 kDa were detected. This identified that the antibody was synthesized and produced correctly.

Example 6

Validation of Affinity of 3C4 Antibody

Figure 8:
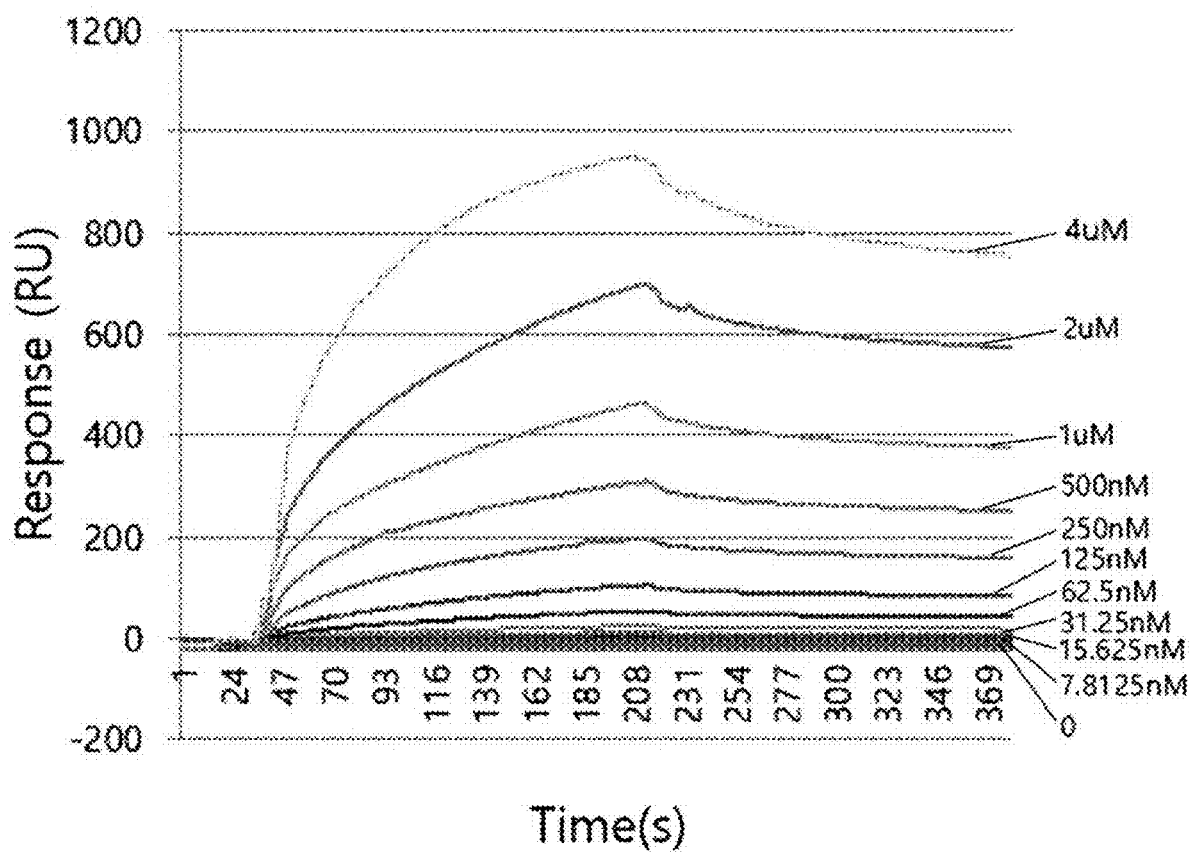
FIG. 8 shows results of surface plasmon resonance (SPR) to identify a SCF binding capacity of a human 3C4 antibody according to the present disclosure.

Surface Plasmon Resonance (SPR) was performed to accurately identify the ability of 3C4 antibodies according to the present disclosure to bind to SCF in a numerical manner. Using SR7500DC (Reichert, USA), 20 µg of human antigen SCF protein used for antibody production was immobilized on PEG (Reichert, USA) chip. Then, anti-SCF antibody according to the present disclosure was applied thereto at a varying concentration manner (0, 7.8125 nM, 15.625 nM, 31.25 nM, 62.5 nM, 125 nM, 250 nM, 500 nM, 1 µM and 2 µM). A $K_D$ value as the affinity to SCF was analyzed using the Scrubber2 program. FIG. 8 shows the analysis result. The $K_D$ value is obtained by dividing a kd value by a ka value. The lower the $K_D$ value, the greater the ability to bind to a target substance.

As shown in FIG. 8, the $K_D$ value was about $18.8 \pm 2 \times 10^{-9}$ M, thus indicating that the 3C4 antibody according to the present disclosure exhibited a strong affinity to SCF.

Example 7

Re-Validation of Ability of 3C4 Antibody to Suppress Angiogenesis Induced by SCF After dispensing 300 µl of Matrigel (Corning, USA) into a 12-well plate, HUVEC was mixed with SCF (50 ng/ml) or SCF (50 ng/ml)+3C4 antibody (10 µg/ml) and then the mixture was added to Matrigel. Then, tube formation of HUVEC was observed (n=10) and the results are shown in FIG. 9.

Figure 9:
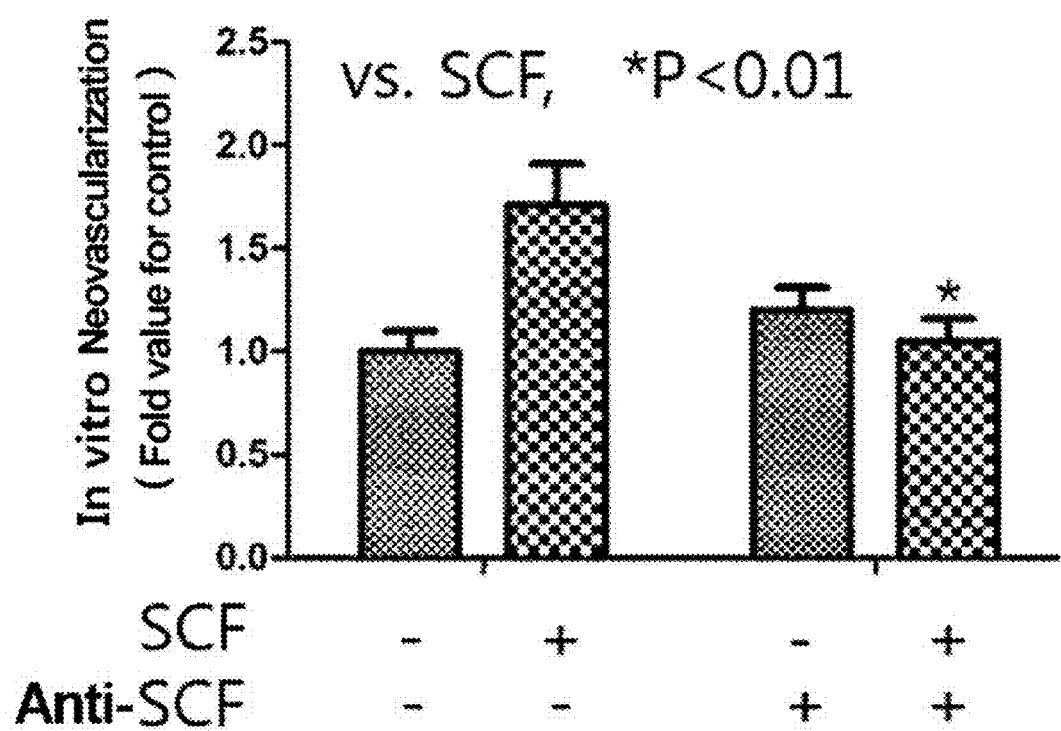
FIG. 9 shows ability of the human 3C4 antibody according to the present disclosure to inhibit vascular endothelial cells (HUVEC) tube formation.

As shown in FIG. 9, it was identified that the 3C4 antibody according to the present disclosure effectively inhibited the tube formation of HUVEC induced by SCF. The results identified that 3C4 antibodies according to the present disclosure could inhibit the neovascularization and thus be useful for the prevention or treatment of angiogenesis-related diseases.

Example 8

Analysis of Ability of 3C4 Antibody to Inhibit C-Kit Phosphorylation Induced by SCF After culturing $6 \times 10^4$ cells for 12 hours, serum depletion was executed for 4 hours. Pretreatment thereof with 3C4 antibody according to the present disclosure was carried out for 15 minutes. Then, after treatment thereof with SCF, the cells were harvested. It was analyzed whether the 3C4 antibody effectively inhibited SCF signaling via c-Kit expression using Western blot. The results are shown in FIG. 10.

Figure 10:
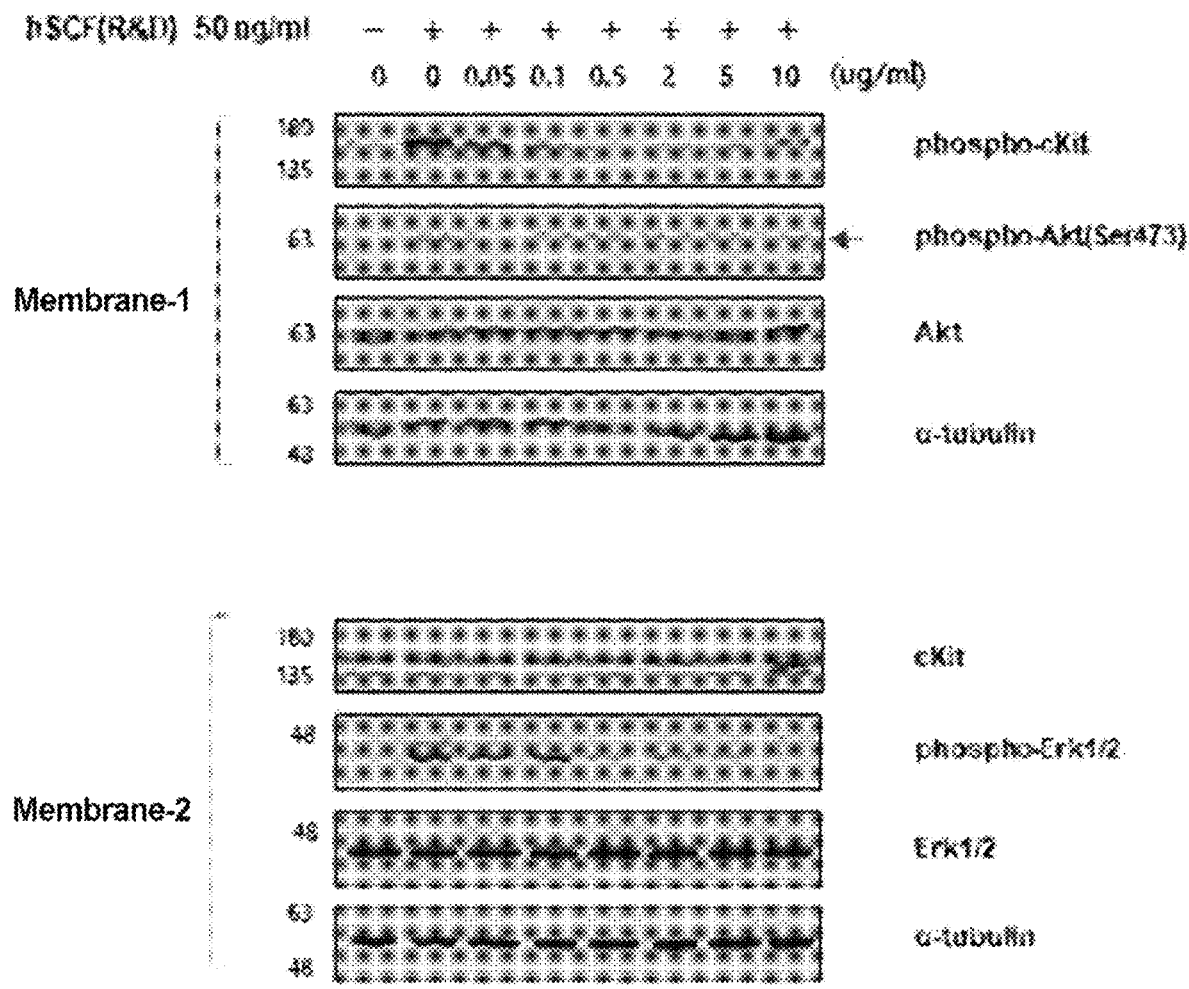
FIG. 10 shows analysis results of c-kit phosphorylation inhibition effect of the human 3C4 antibody according to the present disclosure.

As shown in FIG. 10, the 3C4 antibodies according to the present disclosure not only inhibit c-kit phosphorylation induced by SCF by effectively neutralizing SCF, but also inhibit phosphorylation of AKT and ERK by affecting the downstream signaling pathway.

Example 9

Identification of Binding Capacity to SCF and Galectin-1 Via Protein Microarray Analysis Protein microarray analysis was performed using a HuProt™ v3.1 human proteome microarray (CDI laboratories) protein chip. First, blocking was performed on the protein chip at room temperature using PBST (pH 7.4) containing 2% BSA and 0.1% Tween 20 for two hours. 2 mg of Biotinylated 3C4 antibody was dissolved in PBST (pH 7.4) containing 2% BSA and 0.1% Tween 20 to induce binding for 8 hours at 4° C., and then the chip was washed three times with PBST. 1 µg (18.9 pmol) of Streptavidin-fluorescence (Alexa-Fluor 532 nm) was sprinkled onto the protein chip, thus inducing binding for 1 hour at 4° C., and then the chip was washed three times with PBST. After the remaining buffer solution was completely removed, the protein chip was frozen at −20° C. and was scanned with a GenePix4100A microarray laser scanner (Molecular Devices). The results are shown in FIG. 11.

Figure 11:
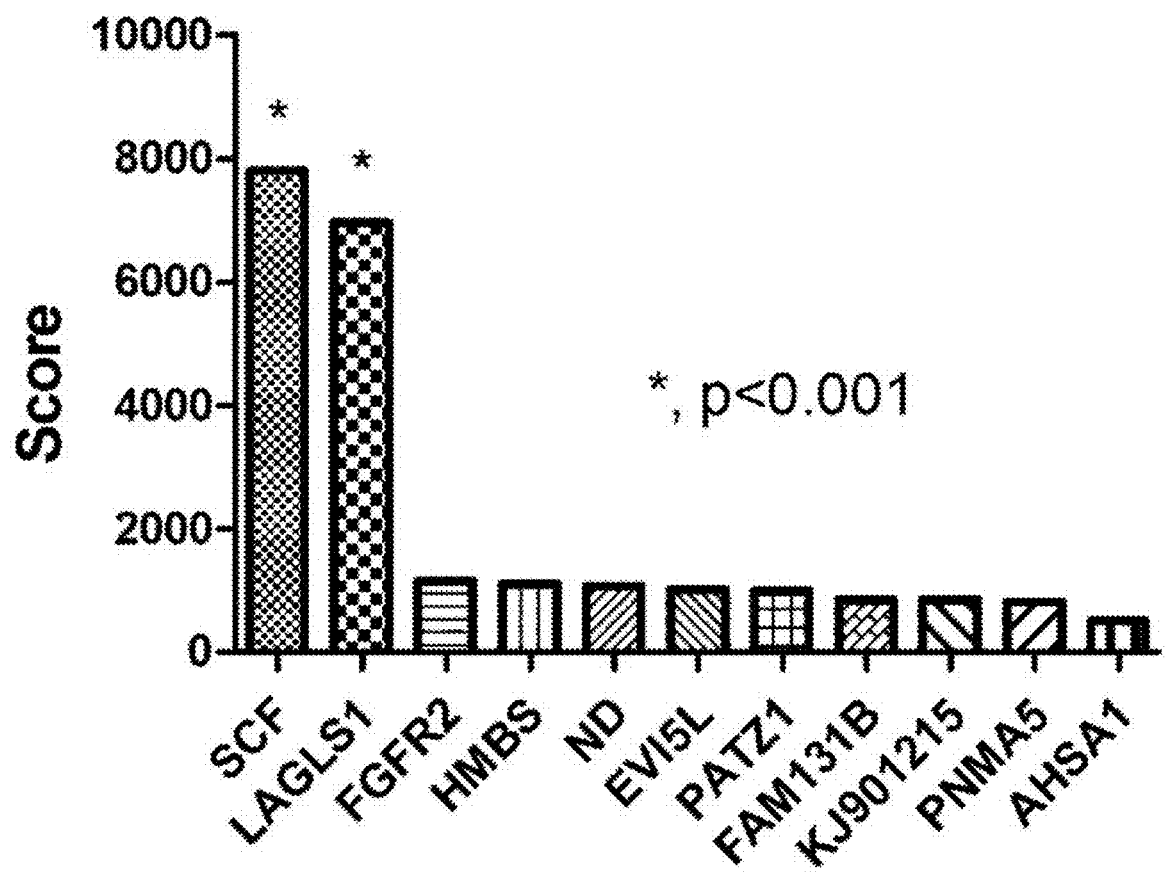
FIG. 11 shows results of protein microarray analysis using the human 3C4 antibody according to the present disclosure.

As shown in FIG. 11, the 3C4 antibody according to the present disclosure exhibited high binding force to galectin-1 (LGALS1) in addition to SCF.

Example 10

Validation of Affinity of 3C4 Antibody to Galectin-1

Figure 12:
FIG. 12 shows results of over-expression of human galectin-1 gene in *Escherichia coli* and then separation and purification of the overexpressed human galectin-1 gene.

Surface Plasmon Resonance (SPR) was performed to accurately identify the ability of the 3C4 antibody according to the present disclosure to bind to galectin-1 in a numerical manner. First, the human galectin-1 (NP 002296.1) gene was cloned into NdeI/BamHI of pET-3a, and overexpressed in *E. coli*, and then separated and purified by ion-exchange chromatography, and then dialyzed with PBS and stored at −70° C. The purified samples were used to identify whether the protein was galectin-1 via SDS-PAGE. The results are shown in FIG. 12.

Figure 13:
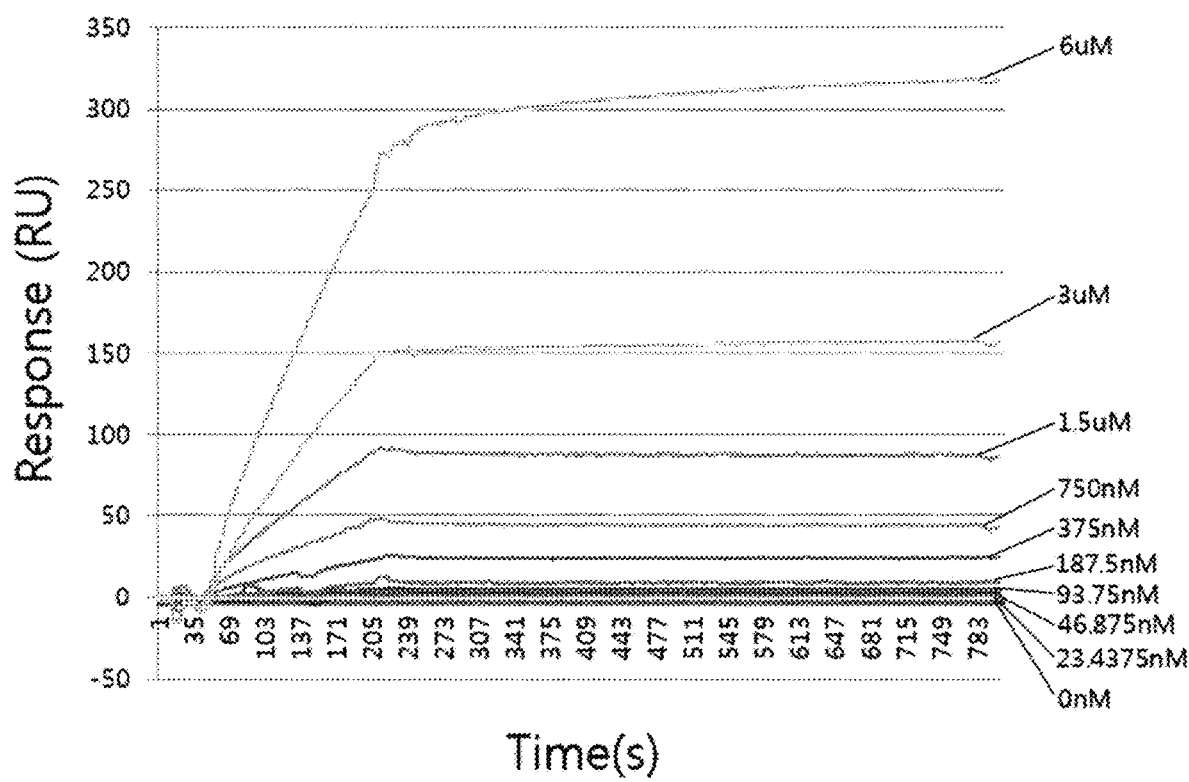
FIG. 13 shows results of surface plasmon resonance (SPR) to identify galectin-1 binding capacity of the human 3C4 antibody according to the present disclosure.

Next, using SR7500DC (Reichert, USA), 20 µg of human antigen galectin-1 protein was immobilized on PEG (Reichert, USA) chip. 3C4 antibodies according to the present disclosure were applied in a concentration varying manner (0, 23.4375 nM, 46.875 nM, 93.75 nM, 187.5 nM, 375 nM, 750 nM, 1.5 µM, 3 µM, and 6 µM). FIG. 13 shows the result of analyzing the $K_D$ value as the affinity to galectin-1, using the Scrubber2 program.

As shown in FIG. 13, the $K_D$ value was about $46.9 \pm 9 \times 10^{-9}$ M, thus indicating that the 3C4 antibody according to the present disclosure exhibited a strong affinity to the galectin-1 as well as SCF.

Example 11

Verification of Ability to Inhibit Angiogenesis Induced by Galectin-1

300 µl of Matrigel (Corning, USA) was dispensed into 12-well plates and then HUVEC was mixed with galectin-1 (5 µg/ml) or galectin-1 (5 µg/ml)+3C4 antibody (5 µg/ml or 10 µg/ml). Then, the mixture was dispensed on Matrigel. Then, tube formation of HUVEC was observed (n=10), and the results are shown in FIG. 14.

Figure 14:
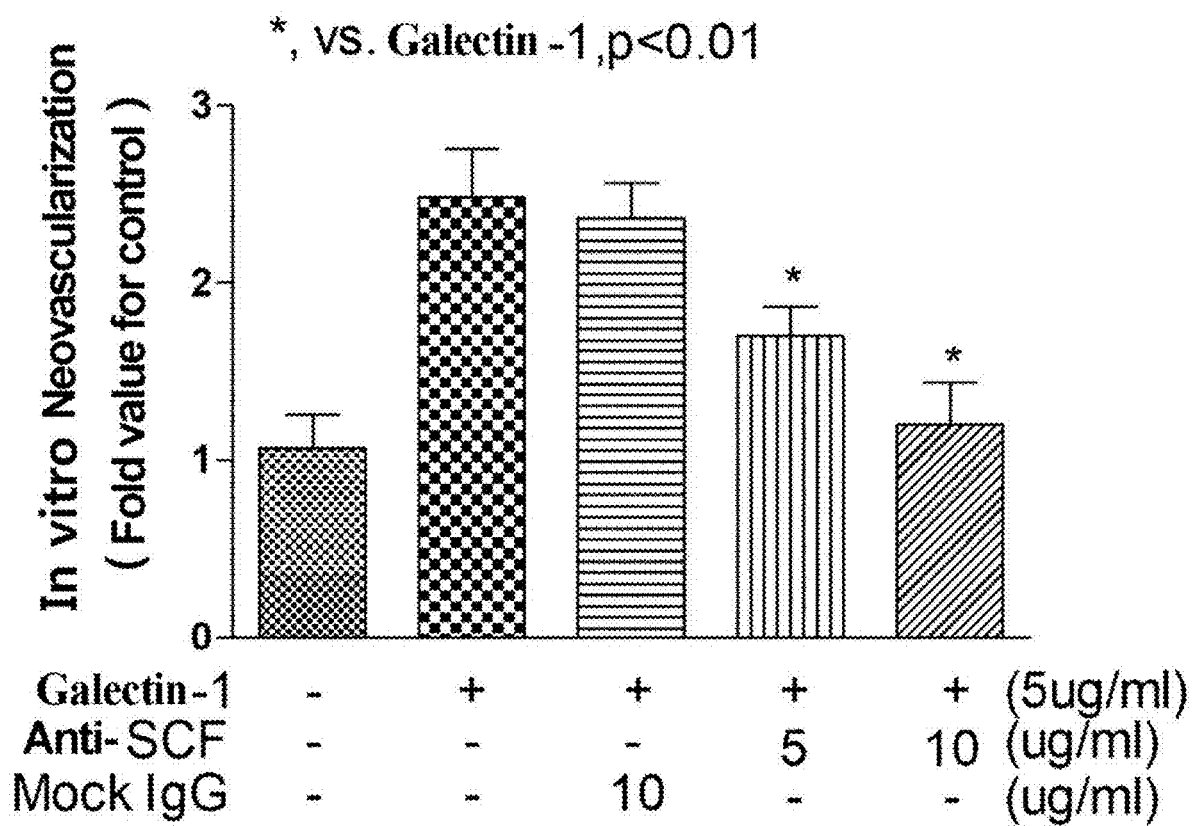
FIG. 14 shows ability of the human 3C4 antibody according to the present disclosure to inhibit the vascular endothelial cell tube formation.

As shown in FIG. 14, it was identified that the 3C4 antibody according to the present disclosure effectively inhibited the tube formation of HUVEC induced by galectin-1. The results suggest that the 3C4 antibody according to the present disclosure is a dual-targeting antibody that inhibits angiogenesis induced by galectin-1 as well as SCF and thus may be usefully used for the prevention or treatment of angiogenesis-related diseases.

Example 12

Verification of Ability to Inhibit Cell Proliferation Induced by SCF and Galectin-1

$5 \times 10^3$ HUVEC cells were dispensed into 96-well plates and incubated for 12 hours using EGM2 medium. Subsequently, the 3C4 antibody according to the present disclosure was applied thereto. Then, the inhibitory effect to suppress the cell proliferation induced by SCF and galectin-1 was scanned using a Celigo Imaging cytometer (Nexcelom Bioscience), and the number of cells was identified by Hoechst staining. The results are shown in FIG. 15.

Figure 15:
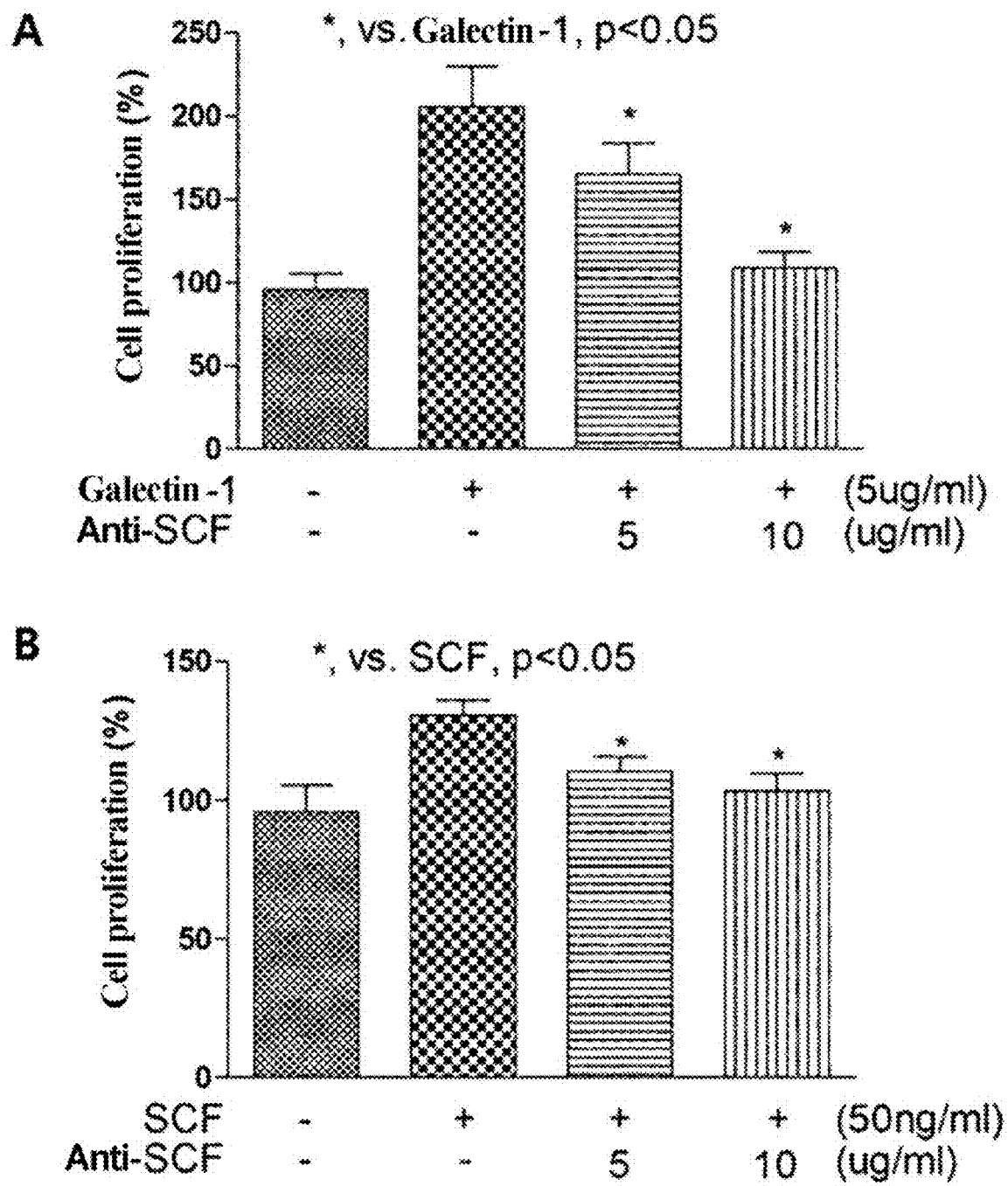
FIG. 15 shows cell proliferation inhibitory effect by galectin-1 (A) and SCF (B) of the human 3C4 antibody according to the present disclosure.

As shown in FIG. 15, it was identified that the proliferation of HUVEC induced by SCF and galectin-1 was inhibited by 3C4 antibody treatment in the concentration-dependent manner. From this result, the 3C4 antibody according to the present disclosure was again identified to effectively inhibit the angiogenesis induced by galectin-1 as well as SCF.

Comparative Example 1

Comparison of Neutralization Ability Between 3C4 Antibody According to Present Disclosure and Polyclonal Antibody of R & D System Experiments were performed to compare the neutralization capacity between commercially available SCF antibodies and the 3C4 antibodies according to the present disclosure. 300 µl of Matrigel (Corning, USA) was dispensed into a 12-well plate and was left for 5 minutes to be solidified. HUVEC was mixed with SCF (50 ng/ml), SCF (50 ng/ml)+ 3C4 antibody or anti-SCF polyclonal antibody (cat #, AF-255-NA) of R & D systems in a concentration varying manner. The mixture was disposed onto Matrigel. Then, tube formation of HUVEC was observed (n=7), and the results are shown in FIG. 16 (*$p<0.05$).

Figure 16:
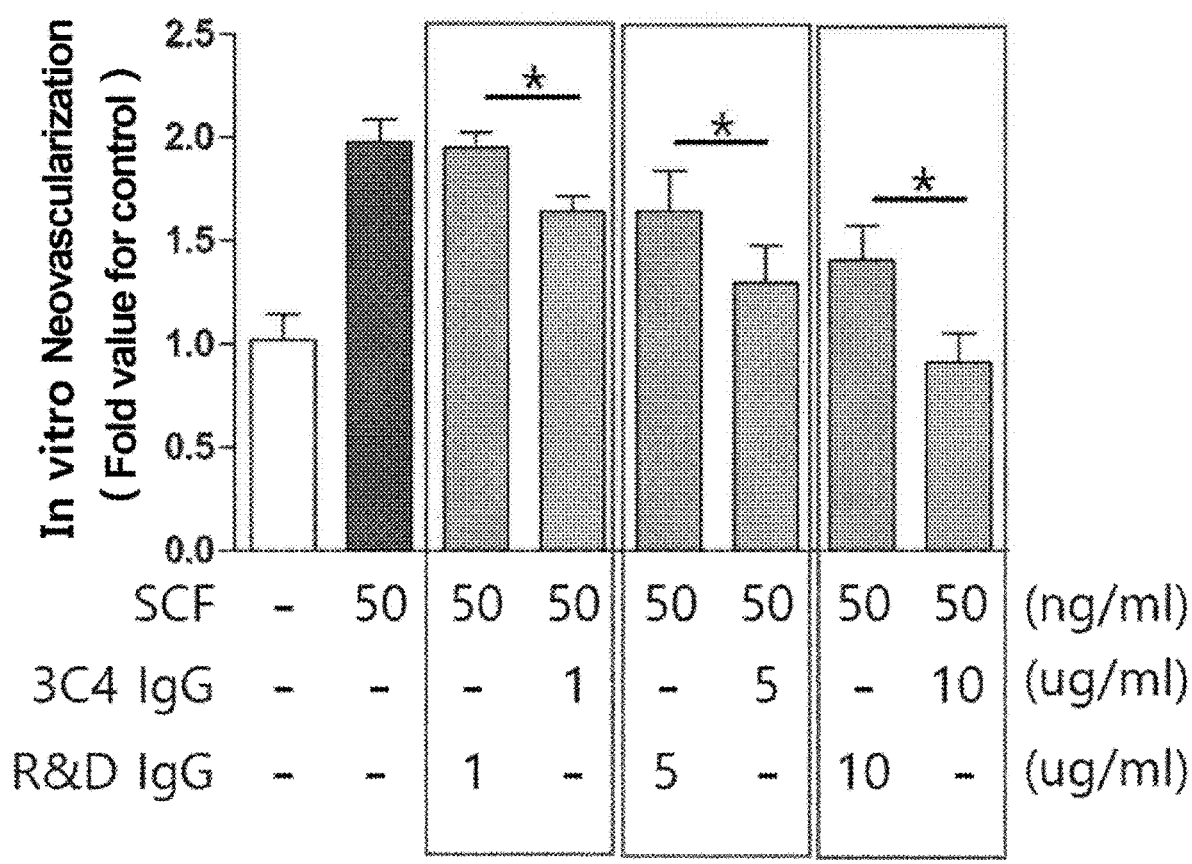
FIG. 16 shows an ability of each of the human 3C4 antibody according to the present disclosure and a commercially available SCF antibody to inhibit tube formation of vascular endothelial cells in order to compare neutralizing capacities of the human 3C4 antibody according to the present disclosure and the commercially available SCF antibody with each other.

As shown in FIG. 16, the 3C4 antibody according to the present disclosure was found to have a significantly higher inhibitory effect on tube formation of HUVEC induced by SCF compared to the anti-SCF polyclonal antibody of R & D systems at all concentrations. It was once again identified from the comparative example that the use of the 3C4 antibody according to the present disclosure significantly inhibited the neovascular expression, compared to the commercially available SCF antibodies, thereby more effectively treating angiogenesis-related disease.

Most of drugs for treatment of the ocular vascular disease target VEGF. However, about 20% of patients are VEGF-non-responsive group. Thus, there is a need to develop new drugs. As identified in the Examples and Comparative Examples, the dual-targeting antibody according to the present disclosure specifically binds to both of the SCF (Stem Cell Factor) and the galectin-1, thereby effectively inhibiting angiogenesis induced by the SCF (Stem Cell Factor) and the galectin-1. Further, the dual-targeting antibody according to the present disclosure may have a treatment effect on patients of VEGF-non-responsive group. Thus, the dual-targeting antibody according to the present disclosure is expected to effectively suppress the abnormal neovascularization when the dual-targeting antibody is co-administrated with existing drugs targeting the VEGF.

Although the present disclosure has been described with reference to the preferred example as mentioned above, the skilled person to the art may make various modifications or variations without departing from the spirit and scope of the disclosure. The appended claims cover any such modifications or variations that fall within the scope of the present disclosure.

What is claimed is:

1. A dual-targeting antibody specifically binding to SCF (Stem Cell Factor) and galectin-1, wherein the dual-targeting antibody comprises:
   a light-chain variable region comprising a light-chain CDR1 comprising the amino acid sequence of SEQ ID NO: 1, a light-chain CDR2 comprising the amino acid sequence of SEQ ID NO: 2, and a light-chain CDR3 comprising the amino acid sequence of SEQ ID NO: 3; and
   a heavy-chain variable region comprising a heavy-chain CDR1 comprising the amino acid sequence of SEQ ID NO: 4, a heavy-chain CDR2 comprising the amino acid sequence of SEQ ID NO: 5, and a heavy-chain CDR3 comprising the amino acid sequence of SEQ ID NO: 6.

2. The dual-targeting antibody of claim 1, wherein the light-chain variable region comprises the amino acid sequence of SEQ ID NO: 7, or the heavy-chain variable region comprises the amino acid sequence of SEQ ID NO: 8.

3. The dual-targeting antibody of claim 1, wherein the dual-targeting antibody comprises the amino acid sequence of SEQ ID NO: 9.

4. The dual-targeting antibody of claim 1, wherein the dual-targeting antibody further comprises a human IgG1-derived invariable region.

5. DNA encoding a dual-targeting antibody specifically binding to SCF (Stem Cell Factor) and galectin-1, wherein the DNA comprises:
   DNA encoding a light-chain variable region comprising nucleotide sequences comprising SEQ ID NO: 10, SEQ ID NO: 11 and SEQ ID NO: 12 respectively encoding a light-chain CDR1 comprising SEQ ID NO: 1, a light-chain CDR2 comprising SEQ ID NO: 2, and a light-chain CDR3 comprising SEQ ID NO: 3; and
   DNA encoding a heavy-chain variable region comprising nucleotide sequences comprising SEQ ID NO: 13, SEQ ID NO: 14 and SEQ ID NO: 15 respectively encoding a heavy-chain CDR1 comprising SEQ ID NO: 4, a heavy-chain CDR2 comprising SEQ ID NO: 5, and a heavy-chain CDR3 comprising SEQ ID NO: 6.

6. The DNA encoding the dual-targeting antibody of claim 5, wherein the DNA encoding the light-chain variable region comprises SEQ ID NO: 16.

7. The DNA encoding the dual-targeting antibody of claim 5, wherein the DNA encoding the heavy-chain variable region comprises SEQ ID NO: 17.

8. The DNA encoding the dual-targeting antibody of claim 5, wherein the DNA encoding the dual-targeting antibody comprises SEQ ID NO: 18.

9. A vector comprising the DNA of one of claims 5 to 8.

10. A cell transformed with the vector of claim 9.

11. The cell of claim 10, wherein the cell is a bacterial or animal cell.

* * * * *

SEQUENCE LISTING

<160> NUMBER OF SEQ ID NOS: 22

<210> SEQ ID NO 1
<211> LENGTH: 11
<212> TYPE: PRT
<213> ORGANISM: Artificial
<220> FEATURE:
<223> OTHER INFORMATION: CDR1 of a light chain variable region of 3C4

<400> SEQUENCE: 1

Gln Ser Leu Val Tyr Ser Asp Gly Asn Thr Tyr
1               5                   10

<210> SEQ ID NO 2
<211> LENGTH: 3
<212> TYPE: PRT
<213> ORGANISM: Artificial
<220> FEATURE:
<223> OTHER INFORMATION: CDR2 of a light chain variable region of 3C4

<400> SEQUENCE: 2

Lys Val Ser
1

```
<210> SEQ ID NO 3
<211> LENGTH: 8
<212> TYPE: PRT
<213> ORGANISM: Artificial
<220> FEATURE:
<223> OTHER INFORMATION: CDR3 of a light chain variable region of 3C4

<400> SEQUENCE: 3

Met Gln Gly Thr His Trp Pro Leu
1               5

<210> SEQ ID NO 4
<211> LENGTH: 8
<212> TYPE: PRT
<213> ORGANISM: Artificial
<220> FEATURE:
<223> OTHER INFORMATION: CDR1 of a heavy chain variable region of 3C4

<400> SEQUENCE: 4

Gly Phe Thr Phe Ser Ser Tyr Gly
1               5

<210> SEQ ID NO 5
<211> LENGTH: 8
<212> TYPE: PRT
<213> ORGANISM: Artificial
<220> FEATURE:
<223> OTHER INFORMATION: CDR2 of a heavy chain variable region of 3C4

<400> SEQUENCE: 5

Ile Trp Tyr Asp Gly Ser Asn Asn
1               5

<210> SEQ ID NO 6
<211> LENGTH: 16
<212> TYPE: PRT
<213> ORGANISM: Artificial
<220> FEATURE:
<223> OTHER INFORMATION: CDR3 of a heavy chain variable region of 3C4

<400> SEQUENCE: 6

Ala Arg Gly Gln Asn Tyr Tyr Gly Leu Gly Ser Tyr Phe Phe Asp Tyr
1               5                   10                  15

<210> SEQ ID NO 7
<211> LENGTH: 111
<212> TYPE: PRT
<213> ORGANISM: Artificial
<220> FEATURE:
<223> OTHER INFORMATION: a light chain variable region of 3C4

<400> SEQUENCE: 7

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
```

Thr His Trp Pro Leu Ser Ala Glu Gly Pro Arg Trp Arg Ser Asn
             100                 105                 110

<210> SEQ ID NO 8
<211> LENGTH: 120
<212> TYPE: PRT
<213> ORGANISM: Artificial
<220> FEATURE:
<223> OTHER INFORMATION: a heavy chain variable region of 3C4

<400> SEQUENCE: 8

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Asp Trp Val
        35                  40                  45

Ala Val Ile Trp Tyr Asp Gly Ser Asn Asn Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Asn Tyr Tyr Gly Leu Gly Ser Tyr Phe Phe Asp Tyr
            100                 105                 110

Trp Gly Gln Gly Thr Leu Val Thr
        115                 120

<210> SEQ ID NO 9
<211> LENGTH: 671
<212> TYPE: PRT
<213> ORGANISM: Artificial
<220> FEATURE:
<223> OTHER INFORMATION: amino acid sequence of 3C4

<400> SEQUENCE: 9

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Ser Ala Glu Gly Pro Arg Trp Arg Ser Asn Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

-continued

Gly Asn Ser Gln Glu Ser Val Thr Glu Gln Asp Ser Lys Asp Ser Thr
            165                 170                 175
Tyr Ser Leu Ser Ser Thr Leu Thr Leu Ser Lys Ala Asp Tyr Glu Lys
        180                 185                 190
His Lys Val Tyr Ala Cys Glu Val Thr His Gln Gly Leu Ser Ser Pro
    195                 200                 205
Val Thr Lys Ser Phe Asn Arg Gly Glu Cys Gln Val Gln Leu Val Glu
210                 215                 220
Ser Gly Gly Gly Val Val Gln Pro Gly Arg Ser Leu Arg Leu Ser Cys
225                 230                 235                 240
Val Ala Ser Gly Phe Thr Phe Ser Ser Tyr Gly Met His Trp Val Arg
                245                 250                 255
Gln Ala Pro Gly Lys Gly Leu Asp Trp Val Ala Val Ile Trp Tyr Asp
            260                 265                 270
Gly Ser Asn Asn Asp Tyr Ala Asp Ser Val Lys Gly Arg Phe Thr Ile
        275                 280                 285
Ser Arg Asp Asn Ser Lys Asn Thr Leu Tyr Leu Gln Met Asn Ser Leu
    290                 295                 300
Arg Ala Glu Asp Thr Ala Val Tyr Tyr Cys Ala Arg Gly Gln Asn Tyr
305                 310                 315                 320
Tyr Gly Leu Gly Ser Tyr Phe Phe Asp Tyr Trp Gly Gln Gly Thr Leu
                325                 330                 335
Val Thr Val Ser Ser Ala Ser Thr Lys Gly Pro Ser Val Phe Pro Leu
            340                 345                 350
Ala Pro Ser Ser Lys Ser Thr Ser Gly Gly Thr Ala Ala Leu Gly Cys
        355                 360                 365
Leu Val Lys Asp Tyr Phe Pro Glu Pro Val Thr Val Ser Trp Asn Ser
    370                 375                 380
Gly Ala Leu Thr Ser Gly Val His Thr Phe Pro Ala Val Leu Gln Ser
385                 390                 395                 400
Ser Gly Leu Tyr Ser Leu Ser Ser Val Val Thr Val Pro Ser Ser Ser
                405                 410                 415
Leu Gly Thr Gln Thr Tyr Ile Cys Asn Val Asn His Lys Pro Ser Asn
            420                 425                 430
Thr Lys Val Asp Lys Lys Val Glu Pro Lys Ser Cys Asp Lys Thr His
        435                 440                 445
Thr Cys Pro Pro Cys Pro Ala Pro Glu Leu Leu Gly Gly Pro Ser Val
    450                 455                 460
Phe Leu Phe Pro Pro Lys Pro Lys Asp Thr Leu Met Ile Ser Arg Thr
465                 470                 475                 480
Pro Glu Val Thr Cys Val Val Val Asp Val Ser His Glu Asp Pro Glu
                485                 490                 495
Val Lys Phe Asn Trp Tyr Val Asp Gly Val Glu Val His Asn Ala Lys
            500                 505                 510
Thr Lys Pro Arg Glu Glu Gln Tyr Asn Ser Thr Tyr Arg Val Val Ser
        515                 520                 525
Val Leu Thr Val Leu His Gln Asp Trp Leu Asn Gly Lys Glu Tyr Lys
    530                 535                 540
Cys Lys Val Ser Asn Lys Ala Leu Pro Ala Pro Ile Glu Lys Thr Ile
545                 550                 555                 560
Ser Lys Ala Lys Gly Gln Pro Arg Glu Pro Gln Val Tyr Thr Leu Pro
                565                 570                 575
Pro Ser Arg Asp Glu Leu Thr Lys Asn Gln Val Ser Leu Thr Cys Leu

```
            580                 585                 590
Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
        610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670
```

<210> SEQ ID NO 10
<211> LENGTH: 33
<212> TYPE: DNA
<213> ORGANISM: Artificial
<220> FEATURE:
<223> OTHER INFORMATION: DNA sequence coding CDR1 of a light chain
      variable region of 3C4

<400> SEQUENCE: 10
caaagcctcg tatacagtga tggaaacacc tac                              33

<210> SEQ ID NO 11
<211> LENGTH: 9
<212> TYPE: DNA
<213> ORGANISM: Artificial
<220> FEATURE:
<223> OTHER INFORMATION: DNA sequence coding CDR2 of a light chain
      variable region of 3C4

<400> SEQUENCE: 11 aaggtttct                                                          9

<210> SEQ ID NO 12
<211> LENGTH: 24
<212> TYPE: DNA
<213> ORGANISM: Artificial
<220> FEATURE:
<223> OTHER INFORMATION: DNA sequence coding CDR3 of a light chain
      variable region of 3C4

<400> SEQUENCE: 12
atgcaaggta cacactggcc tctt                                        24

<210> SEQ ID NO 13
<211> LENGTH: 24
<212> TYPE: DNA
<213> ORGANISM: Artificial
<220> FEATURE:
<223> OTHER INFORMATION: DNA sequence coding CDR1 of a heavy chain
      variable region of 3C4

<400> SEQUENCE: 13
ggattcacct tcagtagcta tggc                                        24

<210> SEQ ID NO 14
<211> LENGTH: 24
<212> TYPE: DNA
<213> ORGANISM: Artificial
<220> FEATURE:
<223> OTHER INFORMATION: DNA sequence coding CDR2 of a heavy chain
      variable region of 3C4

<400> SEQUENCE: 14
atatggtatg atggaagtaa taac                                       24

<210> SEQ ID NO 15
<211> LENGTH: 48
<212> TYPE: DNA
<213> ORGANISM: Artificial
<220> FEATURE:
<223> OTHER INFORMATION: DNA sequence coding CDR3 of a heavy chain
      variable region of 3C4

<400> SEQUENCE: 15
gcgagagggc aaaattacta tggtttgggg agttatttct ttgactac              48

<210> SEQ ID NO 16
<211> LENGTH: 333
<212> TYPE: DNA
<213> ORGANISM: Artificial
<220> FEATURE:
<223> OTHER INFORMATION: DNA sequence coding a light chain variable
      region of 3C4

<400> SEQUENCE: 16
gatgttgtga tgactcagtc tccactctcc ctgcccgtca cccttggaca gccggcctcc  60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
ctttcggcgg agggaccaag gtggagatca aac                             333

<210> SEQ ID NO 17
<211> LENGTH: 360
<212> TYPE: DNA
<213> ORGANISM: Artificial
<220> FEATURE:
<223> OTHER INFORMATION: DNA sequence coding a heavy chain variable
      region of 3C4

<400> SEQUENCE: 17
caggtgcagc tggtggagtc tgggggaggc gtggtccagc ctggaggtc cctgagactc   60 tcctgtgtag cgtctggatt caccttcagt agctatggca tgcactgggt ccgccaggct 120
ccaggcaagg ggctggactg ggtggcagtt atatggtatg atggaagtaa taacgactat 180
gcagactccg tgaagggccg attcaccatc tccagagaca attccaagaa cacactgtat 240
ctacaaatga acagcctgag agccgaggac acggctgtat attactgtgc gagagggcaa 300
aattactatg gtttggggag ttatttcttt gactactggg gccagggaac cctggtcacc 360

<210> SEQ ID NO 18
<211> LENGTH: 2019
<212> TYPE: DNA
<213> ORGANISM: Artificial
<220> FEATURE:
<223> OTHER INFORMATION: DNA sequence coding 3C4

<400> SEQUENCE: 18
gatgttgtga tgactcagtc tccactctcc ctgcccgtca cccttggaca gccggcctcc  60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240

```
agcagggtgg aggctgagga tgttggggtt tattactgca tgcaaggtac acactggcct    300
ctttcggcgg agggaccaag gtggagatca aaccgtacgg tggctgcacc atctgtcttc    360
atcttcccgc catctgatga gcagttgaaa tctggaactg cctctgttgt gtgcctgctg    420
ataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgagctc gcccgtcaca aagagcttca caggggaga gtgttgacag    660
gtgcagctgt tggagtctgg gggaggcgtg gtccagcctg ggaggtccct gagactctcc    720
tgtgtagcgt ctggattcac cttcagtagc tatggcatgc actgggtccg ccaggctcca    780
ggcaaggggc tggactgggt ggcagttata tggtatgatg aagtaataa cgactatgca    840
gactccgtga agggccgatt caccatctcc agagacaatt ccaagaacac actgtatcta    900
caaatgaaca gcctgagagc cgaggacacg gctgtatatt actgtgcgag agggcaaaat    960
tactatggtt tgggagtta tttctttgac tactggggcc agggaaccct ggtcaccgtc    1020
tcctcagcct ccaccaaggg cccatcggtc ttccccctgg cacctcctc caagagcacc    1080
tctgggggca gcggccct gggctgcctg gtcaaggact acttccccga accggtgacg    1140
gtgtcgtgga actcaggcgc cctgaccagc ggcgtgcaca ccttcccggc tgtcctacag    1200
tcctcaggac tctactccct cagcagcgtg gtgaccgtgc cctccagcag cttgggcacc    1260
cagacctaca tctgcaacgt gaatcacaag cccagcaaca ccaaggtgga caagaaagtt    1320
gagcccaaat cttgtgacaa aactcacaca tgcccaccgt gcccagcacc tgaactcctg    1380
gggggaccgt cagtcttcct cttccccca aaacccaagg acaccctcat gatctcccgg    1440
accctgagg tcacatgcgt ggtggtggac gtgagccacg aagaccctga ggtcaagttc    1500
aactggtacg tggacggcgt ggaggtgcat aatgccaaga caaagccgcg ggaggagcag    1560
tacaacagca cgtaccgtgt ggtcagcgtc ctcaccgtcc tgcaccagga ctggctgaat    1620
ggcaaggagt acaagtgcaa ggtcagcaac aaagccctcc cagcccccat cgagaaaacc    1680
atctccaaag ccaaagggca gccccgagaa ccacaggtgt acaccctgcc cccatcccgg    1740
gatgagctga ccaagaacca ggtcagcctg acctgcctgg tcaaaggctt ctatcccagc    1800
gacatcgccg tggagtggga gagcaatggg cagccggaga caactacaa gaccacgcct    1860
cccgtgctgg actccgacgg ctccttcttc ctctacagca agctcaccgt ggacaagagc    1920
aggtggcagc aggggaacgt cttctcatgc tccgtgatgc atgaggctct gcacaaccac    1980
tacacgcaga agagcctctc cctgtctccg ggtaaatga                          2019
```

<210> SEQ ID NO 19
<211> LENGTH: 27
<212> TYPE: DNA
<213> ORGANISM: Artificial
<220> FEATURE:
<223> OTHER INFORMATION: light chain forward primer

<400> SEQUENCE: 19
cagctcctgg ggctgctaat gctctgg                                        27

<210> SEQ ID NO 20
<211> LENGTH: 24
<212> TYPE: DNA
<213> ORGANISM: Artificial
<220> FEATURE:

```
<223> OTHER INFORMATION: light chain reverse primer

<400> SEQUENCE: 20
cagttgctaa ctgttccgtg gatg                                              24

<210> SEQ ID NO 21
<211> LENGTH: 26
<212> TYPE: DNA
<213> ORGANISM: Artificial
<220> FEATURE:
<223> OTHER INFORMATION: heavy chain forward primer

<400> SEQUENCE: 21
atggarttgg ggctgwgctg ggtttt                                            26

<210> SEQ ID NO 22
<211> LENGTH: 24
<212> TYPE: DNA
<213> ORGANISM: Artificial
<220> FEATURE:
<223> OTHER INFORMATION: heavy chain reverse primer

<400> SEQUENCE: 22
acttttgaga gcagttccag gagc                                              24
```